United States Patent
Park et al.

(10) Patent No.: US 9,334,326 B2
(45) Date of Patent: *May 10, 2016

(54) ANTIBODY THAT BINDS DOMAIN 2 OF ICAM-1 AND METHODS OF TREATMENT

(71) Applicant: SNU R&DB FOUNDATION, Seoul (KR)

(72) Inventors: Seong Hoe Park, Seoul (KR); Kyeong Cheon Jung, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/428,274

(22) PCT Filed: Oct. 11, 2012

(86) PCT No.: PCT/KR2012/008240
§ 371 (c)(1),
(2) Date: Mar. 13, 2015

(87) PCT Pub. No.: WO2014/042305
PCT Pub. Date: Mar. 20, 2014

(65) Prior Publication Data
US 2015/0252111 A1    Sep. 10, 2015

(30) Foreign Application Priority Data

Sep. 14, 2012 (KR) .................. 10-2012-0101917

(51) Int. Cl.
| | | |
|---|---|---|
| *A61K 39/395* | (2006.01) | |
| *C07K 16/28* | (2006.01) | |
| *A61K 45/06* | (2006.01) | |
| *C07K 16/46* | (2006.01) | |
| *A61K 39/00* | (2006.01) | |

(52) U.S. Cl.
CPC ......... *C07K 16/2821* (2013.01); *A61K 39/3955* (2013.01); *A61K 45/06* (2013.01); *C07K 16/46* (2013.01); *A61K 2039/505* (2013.01); *C07K 2317/24* (2013.01); *C07K 2317/35* (2013.01); *C07K 2317/51* (2013.01); *C07K 2317/515* (2013.01); *C07K 2317/60* (2013.01)

(58) Field of Classification Search
None
See application file for complete search history.

(56) References Cited

U.S. PATENT DOCUMENTS 7,696,323 B2    4/2010  Bredehorst et al.
8,900,586 B2 *  12/2014 Park .................. C07K 16/2821
                                                        424/130.1

FOREIGN PATENT DOCUMENTS

EP          0459577 A3     12/1991
KR          20110023897    3/2011

OTHER PUBLICATIONS

Rudikoff et al., Proc Natl Acad Sci USA 79: 1979-1983 (1982).*
Colman, Research in Immunology 145: 33-36 (1994).*
Kussie et al., (J. Immunol. 152: 146-152 (1994).*
Chen et al., EMBO J., 14: 2784-2794 (1995).*
Attwood, Science 290:471-473 (2000).*
Skolnick et al., Trends in Biotech. 18: 34-39 (2000).*
Cosimi et al "In Vivo Effects of Monoclonal Antibody to ICAM-1 (CD54) in Nonhuman Primates With Renal Allografts", The Journal of Immunology, vol. 144.4604-4612, No. 12. Jun. 15, 1990.
Morelli et al "Tolerogenic dendritic cells and the quest for transplant tolerance", Nature Publishing Group, www.nature.com/reviews/immunol, pp. 610-612, Aug. 2007, vol. 7.
Salmela et al "A Randomized Multicenter Trial of the Anti-ICAM-1 Monoclonal Antibody (ENLIMOMAB) for the Prevention of Acute Rejection and Delayed Onset of Graft Function in Cadaveric Renal Transplantation: A Report of the European Anti-ICAM-1 Renal Transplant Study Group", Issue: vol. 67(5), Mar. 15, 1999, pp. 729-736.
Sousa "Dendritic cells in a mature age" Nature Publishing Group, www.nature.com/reviews/immunol, pp. 476-483, Jun. 2006, vol. 6.
Steinman et al "Tolerogenic Dendritic Cells", Annu. Rev. Immunol. 2003. 21:685-711.

* cited by examiner

*Primary Examiner* — Phillip Gambel
(74) *Attorney, Agent, or Firm* — Vorys, Sater, Seymour and Pease LLP; Mih Suhn Koh

(57) ABSTRACT

Disclosed are a monoclonal antibody targeting domain 2 of ICAM-1 protein and a composition comprising the monoclonal antibody for treating or preventing T cell-mediated immune disease. The antibody of the present application induces antigen-specific T cell tolerance through the regulation of dendritic cell differentiation, and therefore, can be effectively used to treat or prevent autoimmune disease, organ or tissue transplant rejection, and graft-versus-host-disease.

13 Claims, 33 Drawing Sheets

ANTIBODY THAT BINDS DOMAIN 2 OF ICAM-1 AND METHODS OF TREATMENT

CROSS-REFERENCE TO RELATED APPLICATIONS

The present application is a national stage application of International Patent Application No. PCT/KR2012/008240, filed Oct. 11, 2012, and claims the benefit of Korean Patent Application No. 2012-0101917, filed Sep. 14, 2012 in the Korean Intellectual Property Office, the disclosure of which are incorporated herein.

STATEMENT OF SEQUENCE LISTING

The Sequence Listing submitted in text format (.txt) named "SequenceListing.txt", created on Mar. 9, 2015 (2.0 KB), is incorporated herein by reference.

DEPOSIT OF MICROORGANISM

The MD-3 antibody recited in this application was deposited in the International Depository Authority on May 5, 2011 as Accession No. KCLRF-BP-00264, as confirmed by a copy of the Certificate of Deposit for the MD-3 attached hereto.

BACKGROUND OF INVENTION

1. Field of the Invention

The present disclosure generally relates to antibodies specific for ICAM-1 and compositions comprising the same and methods for treating related disease using the same.

2. Description of the Related Art

Tolerance to specific antigens is the ultimate therapeutic goal in two major immunological fields, autoimmunity and transplantation rejection. Over the past several decades, the generation of a large array of immunosuppressive agents has increased the number of therapeutic tools available to address these two issues. The focus has now shifted to tackling the side effects of long-term immunosuppression. The final goal is to achieve T and B cell tolerance that is antigen specific without the need for long-term generalized immunosuppression.

According to the mechanisms underlying peripheral T cell tolerance upto now, DCs (Dendritic Cells) have a key role in immune regulation (Steinman et al., 2003. Annu. Rev. Immunol. 21:685-711) and antigen presentation by immature and semimature DCs results in immune tolerance rather than effective T cell immunity because of the failure to provide sufficient co-stimulatory signals (Reis e Sousa, 2006. Nat. Rev. Immunol. 6: 476-483). These tolerogenic DCs are characterized by low-level expression of surface MHC molecules and several other co-stimulatory receptors and the production of low levels of Th1 cytokines, notably IL-12p70 (Morelli and Thomson, 2007. Nat. Rev. Immunol. 7: 610-621).

ICAM-1 is a cell surface glycoprotein and a member of the immunoglobulin superfamily composed of five extracellular immunoglobulin-like domains) and expresses at low level in various types of cells but the expression is greatly increased in the inflammatory region. ICAM-1 binds to LFA-1 (Leukocyte Function Associated Antigen-1) expressed on the surface of T cells, and functions as a costimulatory factor for antigen presenting cells thus medicating the interaction between antigen presenting cells such as DC and T cells (Transplantation. 1999, 67:729-736). Also the expression of ICAM-1 is increased at the inflammatory site of endothelial cells of blood vessels and is involved in the migration of leukocytes to the inflammatory site.

Thus several antibodies to ICAM-1 have been developed to regulate the inflammatory and immunological response. Among them is an IgG2a mAb R6.5 (BIRR-1, Enlimomab). It has been found that it inhibits the adhesion of leukocytes to endothelial cells of the blood vessel thus reducing the extravasation of leukocytes into tissue and the damages to the inflammatory tissues (J Immunol. 1990, 144: 4604-4612). However, Enlimomab has been found to have side effects such as fever and leukocytopenia and not to able to reduce the rate of acute rejection or the risk of delayed onset of graft function after renal transplantation in a randomized multicenter study (Transplantation 1999, 67:729-736).

European patent application 0 459 577 discloses an antibody to ICAM-1 inhibiting the adhesion of rhinovirus to cellular receptors. U.S. Pat. No. 7,696,324 discloses a humanized antibody of what is disclosed in EP 0 459 577.

ICAM-1 plays a key role in the defense to bacterial infection by host cells since its role in the migration of leukocytes through endothelial cells in the initiation of immunological response. Therefore there are needs to develop antibodies based on the immunological regulation via the interaction between T cells and antigen presenting cells without affecting the migration of leukocytes through endothelial cells of the blood vessel.

SUMMARY OF THE INVENTION

In one aspect, the present disclosure provides a monoclonal antibody or an antigen-binding fragment thereof specific for human ICAM-1, the monoclonal antibody comprising: at least one complementary determining regions (CDRs) from the heavy chain of an antibody produced by the hybridoma cell deposited as accession number of KCLRF-BP-00264 or at least one CDRs from the light chain of an antibody produced by the hybridoma cell deposited as accession number of KCLRF-BP-00264, or both.

In one embodiment, the antibody or antigen-binding fragment thereof comprises two full length heavy chains and two full length light chains.

In other embodiment, the antigen-binding fragment comprises SCV, ScFv, Fv, Fab, Fab', or F(ab')$_2$.

In other embodiment, the antibody or the antigen-binding fragment thereof is characterized by multi-specific, multi-valent or multi-functional.

In other embodiment, the antibody or the antigen-binding fragment thereof is a multimer which is formed by two or more of the antibody or antigen-binding fragment thereof which are identical or different being linked to each other.

In other embodiment, the antibody or the antigen-binding fragment thereof is a chimeric form or humanized form.

In other aspect, the present disclosure provides a pharmaceutical composition comprising the antibody or the antigen binding fragment thereof for treating or preventing T-cell mediated immunological disorder or condition.

In one embodiment, the T-cell mediated immunological disorder or condition is a rejection of a tissue or an organ transplantation rejection, a graft-versus-host disease, antidrug antibody suppression or an autoimmune disease.

In other embodiment, the tissue or the organ transplantation includes pancreatic islet transplantation.

In other embodiment, the tissue or the organ use for the transplantation is an allogenic or xenogenic origin.

In still other embodiment, the pharmaceutical composition further comprises at least one immune-regulatory agent which is T-cell independent.

In still other embodiment, the at least one immune-regulatory agent which is not T-cell dependent is rapamycin, anti-CD154 antibody, or anti-CD40 antibody.

In other aspect, the present disclosure provides hybridoma cell deposited as accession number of KCLRF-BP-00264.

In a further aspect, the present disclosure provides a method for producing antibody specific for ICAM-1 using the hybridoma cell according to the present disclosure.

In a further aspect, the present disclosure provides a composition for regulating the differentiation of a dendritic cell comprising the antibody or the antigen-binding fragment thereof according to the present disclosure.

In one embodiment, the dendritic cell is maintained at a semi-maturated state by the present antibody or the composition comprising the same.

In a further aspect, the present disclosure provides a method for regulating the differentiation of a dendritic cell comprising contacting the antibody or the antigen-binding fragment thereof with an immature dendritic cell in vitro.

In a further aspect, the present disclosure provides a method for treating or preventing T-cell mediated immunological disorder or condition by administering to a subject in need thereof an effective amount of the antibody or the antigen-binding fragment thereof or the composition comprising the same.

The foregoing summary is illustrative only and is not intended to be in any way limiting. Additional aspects and/or advantages of the invention will be set forth in part in the description which follows and, in part, will be obvious from the description, or may be learned by practice of the invention.

Advantageous Effects

The present antibody is able to induce antigen specific T cell tolerance through modulating the differentiation of immature DC to semi-mature DC. The present antibody can suppress the immune response against transplanted tissues without affecting the immune response in general such as the migration of immune cells through the endothelial cells. Thus the present antibody can be used advantageously for suppressing the rejection of transplanted cells or organs, and graft versus host disease or for treating or preventing immune disorders. This obviates the need for the administration of immunosuppressants, or is able to minimize the amount and types of the immunosuppressants in a combination therapy.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 1A is the results from flow cytometry of HEK293 cells transfected with vector alone or vector encoding ICAM-1 domains 1, 2, or 3-5 of human or mouse as shown in the upper panel.

FIG. 1B is the results from monocytes or neutrophils incubated with human umbilical vein endothelial monolayers in the absence (negative control [NC]) or presence of monoclonal antibodies specific for CD18 (IB4) or ICAM-1 (R6.5) with MD-3 to test the adhesion of the cells to HUVECs.

FIG. 2A represents the percentage of human HLA-ABC+ or CD3+ cells in the peripheral blood of consecutively analyzed mice at the indicated weeks after transplantation of human CD34+ hematopoietic cells.

FIG. 2B is the flow cytometry data and shows CD4+CD3+ or CD8+CD3+ T cells, B cells (CD19+), monocytes (CD14+), and conventional (CD11c+) or plasmacytoid (CD123+) DCs in the spleen.

FIG. 2C is the flow cytometry data showing the individual population of CD14+CD15− monocytes and CD14−CD15+ neutrophils in the peripheral blood.

FIG. 3A is a schematic representation of experimental protocol.

FIG. 3B is the graphs showing the fasting blood glucose (open circles; right y axis) and porcine C-peptide (closed squares; left y axis) levels monitored weekly.

FIG. 3C is the graph based on serum level of porcine C-peptide, functional survival of islet xenografts plotted over time. The dotted line indicates the day when a portion of the mice were sacrificed for ELISPOT and histopathological analyses.

FIG. 3D is the images of serial kidney sections of a representative mouse in the control or MD-3-treated groups stained with H&E or antibodies specific for insulin, human CD3, or human CD68. Bar represents 100 μm.

FIG. 4A represents the results of ELISPOT assay to assess antigen-specific T tolerance in humanized mice in which the mice were received the islet graft, some recipient mice were challenged with KLH at 4 weeks after transplant and then splenocytes were isolated at 6 weeks after transplant and tested for recall IL-2 and IFN-gamma responses against donor islets, human allogeneic blood mononuclear cells (MLR), and KLH.

FIG. 4B is the summarized data from 4-11 mice presented as total numbers of cytokine-producing cells per $3 \times 10^5$ splenocytes. As a negative control (NC) for anti-islet response, splenocytes from humanized mice that did not undergo transplantation (ungrafted) were stimulated with porcine islets. Splenocytes from engrafted mice cultured in the absence of stimulating antigen (responder only) were used as a negative control for MLR and anti-KLH responses. Horizontal bars represent mean values. Ab, antibody.

FIG. 5A is the results from flow cytometry in which expression levels of MHC class I and II, CD80, CD86, and CD40 on their surface were examined.

FIG. 5B shows the representative cytokine levels in the culture supernatants of immature and LPS-treated monocyte-derived DCs in the presence of MD-3 or control antibody.

FIG. 5C shows the results from humanized mice which were received MD-3 or control antibody three times before LPS (100 μg/mouse) after which splenocytes were isolated 1 d after LPS injection and stained with HLA-ABC, CD11c, CD80, and CD86 antibodies. Representative dot plots of CD80 and CD86 expression on gated CD11c+ DCs are shown at the left. Numbers indicate the percentage of cells in each quadrant. The bar graph in the middle represents the expression level of CD80 and CD85 expressed on the surface of HLA-ABC+CD11c+ of spleen in mice received MD-3 and control mice. The bar graph in the right represents the percentage of CD11c+ cells among the HLA-ABC+ cells in the spleen.

FIG. 6A is a schematic representation of experimental procedure.

FIG. 6B is the results of flow cytometric analysis on the indicated days after islet transplantation to assess depletion of CD11c+DCs in the spleen of humanized mice.

FIG. 6C is the results of T cell response in which splenocytes were isolated 14 d after KLH immunization and tested for recall IL-2 and IFN-gamma responses via ELISPOT assay against donor islets and KLH. The data from individual mice are presented as total numbers of cytokine producing cells per $3 \times 10^5$ splenocytes or normalized anti-islet response (Islet/KLH) by dividing the anti-islet spot number by the anti-KLH spot number in each mouse. Horizontal bars represent mean values.

FIG. 6D is the results from cytometric analysis in which splenocytes from each mouse were stained with anti-human CD11c and anti-HLA-ABC antibodies, and the total number of CD11c+DCs was calculated after flow cytometric analysis. Error bars indicate SE.

FIG. 7A is the flow cytometric results in which HEK293 cells were transfected with Rhesus ICAM-1 gene or chimeric genes of Rhesus and mouse ICAM-1, and MD-3 binding was assessed by flow cytometry (solid line). As the negative control (dotted line), the cells were stained with only FITC-conjugated secondary antibody.

FIG. 7B is the result of islet xenotransplantation in which adult porcine islets (50,000 IEQs/kg) were intraportally transplanted into three Rhesus monkeys (R043, R042, and R038) that received MD-3 antibody alone. PBMCs were isolated on the indicated days after transplantation, and the frequency of T cells secreting IL-2 or IFN-gamma in response to donor islets was determined by ELISPOT assay. Results are presented as numbers of cytokine producing cells per $2.5 \times 10^5$ PBMCs in each triplicate culture. R, responder cells only; R+S, responder cells stimulated with porcine islet cells; (−), negative control responder cells from unsensitized monkeys stimulated with porcine islet cells; (+), positive control responder cells from sensitized monkeys stimulated with porcine islet cells. Error bars indicate SE.

FIG. 7C is the results from ELISA in which anti-Gal IgG levels were measured at the indicated time before and after porcine islet transplantation.

FIG. 8A shows the blood glucose level and serum porcine C-peptide concentration measured at the indicated time after porcine islet transplantation in which Rhesus monkey was induced type 1 diabetes via STZ administration, and then hyperglycemia was controlled by s.c. injecting human recombinant insulin (Exotic insulin). Adult porcine islets (100,000 IEQs/kg) were intraportally transplanted into Rhesus monkeys (R052 and R049) that received MD-3 combined with rapamycin and anti-CD154 antibody.

FIG. 8B is the result from experiment in which PBMCs were isolated at 127 and 7 d after transplantation from R052 and R049, respectively, and the frequency of T cells secreting IL-2 or IFN-gamma in response to donor islets (I) or allogeneic PBMCs (A) was determined by ELISPOT assay. Results are presented as numbers of cytokine-producing cells per $5 \times 10^5$ PBMCs in each triplicate culture. R, responder cells only; R+I, responder cells stimulated with porcine islet cells; R+A, responder cells stimulated with allogeneic PBMCs; (−), unsensitized monkeys as a negative control; (+), sensitized monkeys as a positive control. Error bars indicate SE.

FIG. 8C is the result of ELISA in which anti-Gal IgG levels were measured at the indicated time before and after porcine islet transplantation.

FIG. 10A is a schematic representation of the experimental procedure.

FIG. 10B is the blood glucose level and serum porcine C-peptide concentration measured at the indicated time in which Rhesus monkey (R063) was induced type 1 diabetes via STZ administration, then received adult porcine islets (100,000 IEQs/kg) intraportally, and treated with MD-3 chimeric antibody, sirolimus and anti-CD154 antibody.

FIG. 10C is the graph showing the amount (IU) of the human recombinant insulin (Exotic insulin) injected by s.c. to control hyperglycemia.

FIG. 10D is the blood glucose level after intravenous glucose tolerance test (IVGTT) in DM, D+35 and Non-DM control.

FIG. 11A is a schematic representation of the experimental procedure.

FIG. 11B is the blood glucose level and serum porcine C-peptide concentration measured at the indicated time in which Rhesus monkey (R039) was induced type 1 diabetes via STZ administration, then received adult porcine islets (100,000 IEQs/kg) intraportally, and treated with MD-3 and sirolimus.

FIG. 11C is the graph showing the amount (IU) of the human recombinant insulin (Exotic insulin) injected by s.c. to control hyperglycemia.

FIG. 11D is the blood glucose level after IVGTT in DM, D+35 and Non-DM control.

DETAILED DESCRIPTION OF THE EMBODIMENTS

Figure 1A:
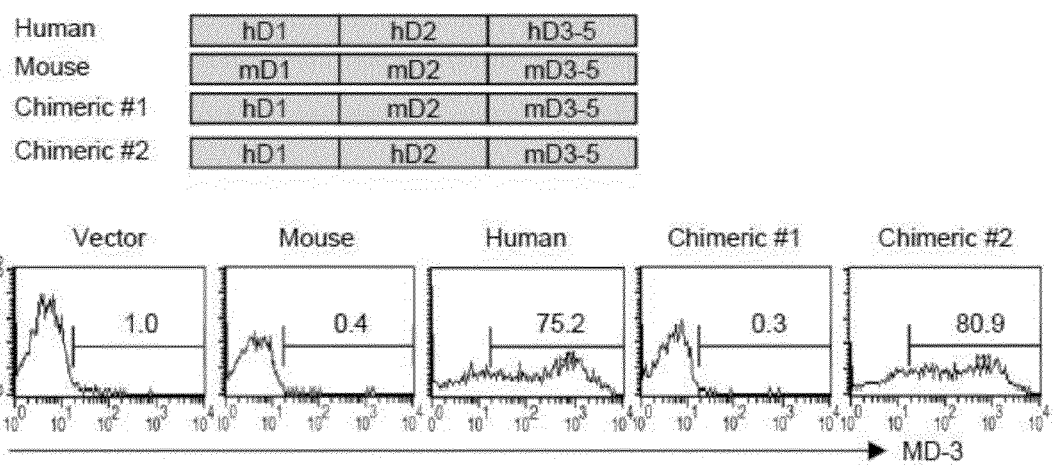
FIGS. 1A and 1B show the characterization results of an anti-human ICAM-1 antibody developed in one embodiment of the present disclosure.

In one aspect, the present disclosure relates to an antibody and antigen-binding fragment thereof recognizing specifically ICAM-1 protein.

ICAM-1 is a cell surface glycoprotein and a member of the immunoglobulin superfamily composed of five extracellular immunoglobulin-like domains numbered 1 to 5 from N to C terminus and expressed at low level in various types of cells but the expression is greatly increased in the inflammatory region. ICAM-1 binds to LFA-1 (Leukocyte Function Associated Antigen-1) expressed on the surface of T cells, and functions as a costimulatory factor for antigen presenting cells thus medicating the interaction between antigen presenting cells such as DC and T cells (Transplantation. 1999, 67:729-736).

The ICAM-1 to which the present antibody specifically recognizes is from mammals, particularly human, non-human primate for example monkeys and chimpanzees. The nucleotide and amino acid sequences of the ICAM-1 are known in the related art. For example, for human, such sequences are known as GenBank Accession No.: NM_000201 and NP_000192 for nucleotide and amino acid sequences respectively. In one embodiment, the present antibody recognizes ICAM-1 from human and non-human primate.

The present antibody specifically recognize particularly domain 2 (D2) from the N terminus of the extracellular region as described above. The present antibody specifically recognizing D2, without being bound by theory, is able to modulate the function and differentiation of dendritic cells (DCs) thus inducing antigen specific T cell tolerance as described hereinafter.

In one embodiment, the present antibody or the antigen-binding fragment thereof comprises at least one complementary determining regions (CDRs) from heavy or light chain produced from the hybridoma cell deposited May 4, 2011 at Korean Cell Line Research Foundation as accession number KCLRF-BP-00264.

The term "antibody" or "Ab" as used herein refers to a protein specifically binding or recognizing other molecules (antigens) through CDRs of light and/or heavy chains and includes types of IgG, IgM, IgA and IgE. Also encompassed in the present antibody or the antigen-binding fragment thereof are monoclonal antibodies having various forms or structures, for example such as intact Abs comprising two heavy chains and two light chains, antigen-binding fragments with or without constant region, chimeric forms, humanized forms, or other genetically modified forms having the properties according to the present invention. In one embodiment, the present antibody is the one produced by the hybridoma cell deposited as KCLRF-BP-00264 deposited May 4, 2011 at Korean Cell Line Research Foundation (address: 28 Yongon-dong, Chongno-Gu, Seoul, 110-744, Korea) as accession number KCLRF-BP-00264. This deposit is available to the public upon grant of a patent disclosing same. In accordance with the United States Code Of Federal Regulations ("CFR") (e.g., 37 CFR §1.808) and The United States Patent And Trademark Office's Manual Of Patent Examination ("MPEP") (e.g., §2410.01), all restrictions on the availability to the public of the deposited material (except as permitted by the CFR and MPEP) will be irrevocably removed upon the granting of any patent issuing from this application or from any related application, including any parent application.

The term "antigen-binding fragment(s)" or "fragment(s)" as used herein refers to a part of the intact antibody as described above and includes ones having an amino acid sequence the length of which is at least one amino acid shorter than the intact one. In terms of functionality, the fragment(s) has at least partial activity or function of the intact antibody and includes for example Fab, Fab', F(ab')$_2$, Fv or Single Chain Antibody (SCA) such as scFv or dsFv, but is not limited thereto.

The term "variable region" as used herein refers to a region in the heavy and light chain to which antigen(s) binds and composed of 4 frames and 3 CDRs (CDR, Complementary Determining Region) showing intense sequence variations among different antibodies.

The term "CDR" as used herein refers to a region that determines the specificity and affinity of an antibody to an antigen and in which the most sequence variations are found. Based on IMCT analysis (http://www.imgt.org/), Each of CDR 1, 2 and 3 of the antibody in one embodiment of the present application, i.e., MD-3 resides in betweens of FR(frame region)1-FR2, FR2-FR3, FR3-JR(joining region) and the sequences of FR1, FR2, FR3 and J region of Kappa light chain and IgG1 heavy chain are known in the related art.

In one embodiment, the present antibody is an antigen-binding fragment comprising at least one CDR from a light chain and/or at least one CDR from a heavy chain, the example of which includes, but is not limited to, Fv, Fab, Fab', or F(ab')$_2$ or SCA (Single Chain Antibody such as scFv.

The fragments may be obtained or prepared using the methods known in the art. For example the antibody fragment may be obtained by treating intact antibodies with a pepsin or a papain. The fragment (Fab')$_2$ may be obtained by treating intact antibodies with pepsin, which can further treated with a thiol reducing agent to produce Fab fragments comprising part of light and heavy chain. Fab fragments can also be obtained by treating intact antibodies with papain. For example, the antibody produced by the present hybridoma may be treated papain or pepsin to prepare Fab or (Fab')$_2$ specifically recognizing ICAM-1.

A Fv (Fragment variable) fragment is composed of the variable regions of a heavy and a light chain in which the variable regions are connected by a covalent or non-covalent bond such as disulfide bond and chemical cross linker (Inbar et al. (1972) PNAS 69:2659). For example, Fv specifically recognizing ICAM-1 may be prepared by treating the antibody produced by the present disclosure with appropriate enzyme to isolate a heavy and light chain thereof or using recombinant DNA technology.

A SCA fragment is an antibody fragment in which variable regions of heavy chain and light chain are connected via a linker such as polypeptide and may be prepared by treating antibody with appropriate enzyme or using recombinant DNA technology known in the art. For example, U.S. Pat. No. 4,936,778 may be referred for preparing ScFv. Or the antibody produced by the present hybridoma cell may be prepared by treating the antibody with appropriate enzymes or using recombinant DNA technology for example by preparing a vector comprising nucleic acids encoding heavy and/or light chain of the antibody and expressing the vector in appropriate cells to prepare antibodies specifically recognizing ICAM-1.

The term "binding" or "specific binding", "specifically binding", "specific recognition" or "specifically recognizing" refers to an affinity of the antibody or the antigen-binding fragment thereof or the composition comprising the same to antigens. In the context of an antigen-antibody binding, "specific binding" refers to a dissociation constant (Kd) which can be differentiated from a non-specific background binding and includes Kd of less than $1\times10^{-5}$M or less than $1\times10^{-6}$M or less than $1 \times 10^{-7}$M. The specific binding may be detected or analyzed using the methods known in the art from example ELISA, immunoprecipitation, or coprecipitation and the like in which appropriate controls to differentiate non-specific from specific bindings are used. In one embodiment, Kd of the present antibody specifically binding to ICAM-1 is $2.78 \times 10^{-8}$ M for a mouse antibody or $8.42 \times 10^{-9}$ M for IgG4 chimeric antibody, which is a sufficiently high affinity so as to be used as a therapeutic antibody.

The present antibody comprising intact antibody or fragments thereof as described above includes multimers such as dimers, trimers, tetramers, pentamers and the like, each of which having all or part of antigen-binding capacity of the monomers. Such multimers also include monomers of homogenous or heterogeneous origin. Multimers includes at least one antigen binding region and thus have an excellent binding affinity to antigens compared to the monomer. Ab multimers may also be used conveniently to prepare multifunctional or multivalent antibodies such as bifunctional or bivalent, trifunctional or trivalent, and tetrafunctional or tetravalent antibodies.

The term "multifunctional" as used herein refers to compositions or antibodies having two or more activities or functions such as antigen binding capacity, enzymatic activity, ligand or receptor binding capacity. In one embodiment, the present antibody may be linked to a polypeptide having enzymatic activity such as luciferase, acetyltransferase, or galactosidase and the like.

Also encompassed in the multifunctional antibodies are multi-specific forms of antibodies such as bivalent, trivalent and the like. By the term "multispecific" or "multivalent", they include variable regions capable of binding to at least two different epitopes, which may be present on the same or different antigens.

The present antibodies include a chimeric or a humanized form of antibody.

The term "humanized form of antibody" as used herein refers to an antibody having CDRs from a donor antibody in the context of a framework of the variable region and constant regions from a human antibody. For example, CDRs from monkey or mouse monoclonal antibodies except residues which are essential for antigen recognition, light and heavy chain frameworks are replaced with those from human antibody. The methods for preparing humanized antibodies are known in the art for example Riechmann, L., et al. (1988) Nature 332:323-327 may be referred.

The term "chimeric form of antibody" refers to an antibody having a variable region i.e., antigen binding region and constant region at least part of which are derived from different species. For example, variable regions are from mice while constant regions are from human. Chimeric antibodies also include class switched antibodies for example from IgG to IgE types. Chimeric forms of antibodies are conventionally prepared by recombinant DNA technology. For example, Moriison, S. I. et al., PNAS USA 81 (1984) 6851-6885 and U.S. Pat. No. 5,202,238 may be referred.

In one embodiment, the present antibody is a chimeric form of antibody which is a human antibody having a light and heavy chain variable region from an antibody produced from the present the hybridoma cell such as for example chimeric antibodies which are grafted onto lambda light chain and IgG4 heavy chain constant region.

In other aspect, the present disclosure relates to a method for producing or preparing ICAM-1 antibody. The present antibody can be produced by a recombinant method or hybridoma cells, particularly deposited as KCLRF-BP-00264.

When recombinant methods are used, nucleic acid sequences encoding a heavy chain and light chain of the present antibody are cloned into a same or a different expression vector which is then transfected into eukaryotic cells for the expression of heavy and light chain proteins. After that, antibodies are obtained from the transfected cells or the media in which the cells are cultured. Such methods for preparing expression vectors, expression of proteins in cells and purifying or isolating proteins of interest from cells are known in the art. For example, Kaufman, R. J., Mol. (2000) Biotechnol. 16:151-160 may be referred. The present antibody may be expressed using vectors comprising nucleic acids encoding the present antibody and cells such as CHO cells, NS0 cells, SP2/0 cells, HEK293 cells, COS cell, yeast or bacterial cells such as E. coli, from which proteins are purified, isolated or obtained from the cell lysates or the media.

The nucleotide sequences encoding all or part of the present antibody may be analyzed using nucleic acids isolated from the hybridoma cells as disclosed herein using conventional methods. Then the isolated nucleic acids are cloned into appropriate vectors which are then transfected into host cells which do not express antibodies such as HEK 293 cells, CHO cells, or NS0 cells to produce a recombinant antibody. The nucleic acids encoding the present antibody or the antigen-binding fragment thereof are cloned into a vector having a promoter, a translational initiation region, a 3' non-translational region, a polyadenylation region and a termination signal. Light and heavy chain may be cloned into a same or a different vector.

For the expression of antibodies using NS0 cells, Barnes, L. M et al., (2000) Cytotechnology 32:109-123 and Norderhaug, L et al., J. Immunol. Methods 204 (1997)77-87 and the like may be referred. For the expression of HEK cells, Schlaeger, E.-J., J. Immunol. Methods 194(1996) 191-199 and the like may be referred.

The present antibody may be isolated from whole cells or the lysates thereof, or cell culture media and purified as a substantially pure form. The purification is to remove by-products of the cells other than antibody of interest such as cell components, nucleic acids, and proteins and the like using methods known in the art such as alkaline/SDS treatments, CsCl separation, column chromatography, and agarose gel electrophoresis. For example, the latest edition of Ausubel F. et al. (eds), Current Protocols in Molecular Biology, Greene Publishing and Wiley Interscience, New York may be referred.

Monoclonal antibodies may be purified from the media of the hybridoma of the present disclosure using methods such as protein A-Sepharose, hydroxyapatite chromatography, dialysis or affinity chromatography.

In other aspects, the present disclosure also relates to a composition comprising the present antibody or the antigen-binding fragment thereof as an active ingredient. The composition may be formulated into a pharmaceutical composition using pharmaceutically acceptable carriers, optionally excipients or stabilizers.

The term "pharmaceutically acceptable carrier" as used herein refers to a physiologically suitable agents such as solvents, dispersing agents, coating agents, antibacterial agents and antifungal agents, isotonic agents, absorption/resorption delaying agents and the like. In one embodiment, carries are used particularly for injections. For example, pharmaceutically acceptable carriers which may be used for the present disclosure, include sterilized aqueous solution or isotonic saline or dispersing agents, and sterilized powders for manufacturing sterile injection liquid. The ordinary people in the related art would be able to select appropriate materials which may be included in the present composition according to the types of active ingredients.

The present antibody or the antigen-binding fragment thereof or the composition comprising the same may be administered using various routes known in the art. It is obvious to the ordinary people in the art that the administration routes or methods may be various depending on the particular efficacies desired. The present antibody or the antigen-binding fragments thereof or the composition comprising the same may be administered through a parenteral delivery such as intravenous, subcutaneous, intramuscular or intraperitoneal injections or delivery through patch, nasal or respiratory patches. In one embodiment, injections are preferred. In particular, parenteral deliveries are preferred. Also the present composition may be formulated in a pharmaceutically acceptable dosage form such as hydrated form such as aqueous solution, or freeze dried form.

The present antibody or the antigen-binding fragment thereof or the composition comprising the same may be advantageously used for treating or preventing or suppressing T cell mediated immune disorders, diseases or conditions.

The term "T cell mediated immune disorders, diseases or conditions" refers to autoimmune diseases, generation of anti-drug antibody, transplantation rejection of cells, tissues or organs of allogenic or heterogenic origin or a graft versus host disease. In one embodiment, the present antibody or the antigen-binding fragment thereof or the composition comprising the same is advantageously used to suppress the rejection of pancreatic islet transplants from allogenic or heterogeneous origin. In other embodiment, the present antibody or the antigen-binding fragment thereof or the composition comprising the same is advantageously used to suppress the rejection of bone-marrow transplantation to treat leukemia. In still other embodiment, the present antibody or the antigen-binding fragment thereof or the composition comprising the same is advantageously used to suppress the rejection of renal transplantation to treat renal diseases.

As used herein, the terms "treat," "treatment," and "treating" include alleviating, abating or ameliorating at least one symptom of a disease or condition which is T cell mediated and/or reducing severity, progression and/or duration thereof, and/or preventing additional symptoms by the administration of the present antibody or the antigen-binding fragment thereof or the composition comprising the same and includes prophylactic and/or therapeutic measures.

As used herein the terms "preventing" or "prevention" refers to prevent or delay the onset or development of at least one symptom of a disease or condition which is T cell mediated by the administration of the present antibody or the antigen-binding fragment thereof or the composition comprising the same compared to non-administered controls.

The present antibody or the antigen-binding fragment thereof or the composition comprising the same may be administered to a subject who has already developed, or is susceptible to or needs a prevention of the diseases or conditions as described above.

As used herein the term, "subject" includes human, non-human primates, and other mammals, particularly subject who is in need of treatment or prevention of T cell mediated diseases or conditions.

Desirable or optimal dosage of the present antibody or the antigen-binding fragment thereof or the composition comprising the same may vary among patients depending on various factors such as body weight, age, sex, general condition of health, diet, severity of diseases, and excretion rate. In one embodiment, it may be administered in amount of about 0.1 to 8 mg/kg of body weight, for example about 1, 2, 3, 4, 5, 6, 7 or 8 mg/kg of body weight. Further, in some cases, it may be administered in an amount of about 10 mg/kg of body weight or about 15 or 20 mg/kg of body weight.

The present antibody or the antigen-binding fragment thereof or the composition comprising the same may be administered in a suitable interval such as daily, weekly or monthly considering half-lives of the antibody or composition administered.

The present antibody or the antigen-binding fragment thereof or the composition comprising the same may administered together with at least one immunosuppressant to control, particularly suppress T cell independent immune reactions of the transplanted cells, tissues or organs. Such T cell independent immunosuppressant includes but is not limited to rapamycin, anti-CD154 antibodies, or anti-CD40 antibodies.

In this perspectives, the present disclosure relates to a method for treating or preventing T cell mediated diseases or conditions comprising administering a therapeutically effective amount of the present antibody or the antigen-binding fragment thereof or the composition comprising the same to a subject in need thereof.

The administration routes, dosages, subjects and T cell mediated diseases are as described hereinbefore. As used herein, the phrase "therapeutically effective amount" when used in connection with the present antibody or the composition comprising the same means an amount of thereof effective for treating, attenuating, reducing the severity of a disease or disorder disclosed herein, reducing the duration of a disease or disorder disclosed herein, prevent the advancement of a disease or disorder disclosed herein, ameliorating one or more symptoms associated with a disease or disorder disclosed herein.

The present antibody or the antigen-binding fragment thereof or the composition comprising the same may be administered alone or in combination with other treatment or other therapeutic agents or immunosuppressants. That is, the present methods may further comprise a step of administering an effective amount of at least one T cell independent immune modulators particularly immunosuppressant. Such T cell independent immunosuppressant which may be used for the combination therapy includes but is not limited to rapamycin, anti-CD154 antibodies, or anti-CD40 antibodies. This is particularly effective since the present antibody or composition induces an antigen specific T cell tolerance through modulating the differentiation of immature DC thus complementing the activity of the present antibody or the composition.

However, such immunosuppressant may not be needed or the amount of administered may be reduced over a period of time. In one embodiment, when the present antibody or the antigen-binding fragment thereof or the composition comprising the same is used to suppress the rejection of allogenic islet transplantation, just one type of immunosuppressant is administered at an early stage of transplantation in comparison to the conventional cases in which generally 2-3 different types of immunosuppressants are used and further the administration of immunosuppressant is ceased after a certain period of time.

In other aspect, the present disclosure relates to a method for modulating the differentiation of dendritic cells in vitro by contacting the present antibody or the composition comprising the same with immature DCs in vitro. Such methods for example may be performed by isolating PBMC from human blood and differentiating DC into a semi-mature state in vitro using the present antibody or the composition and injecting the same to the subject in need of the treatment. In this aspect, the present disclosure further relates to a method to treat or prevent T cell mediated disease ex vivo by administering semi-mature state DCs which are differentiated from PBMCs isolated from the blood using the present antibody or the antigen-binding fragment thereof or the composition comprising the same.

The present disclosure is further explained in more detail with reference to the following examples. These examples, however, should not be interpreted as limiting the scope of the present invention in any manner.

EXAMPLES

Experimental Animals

NOG mice were obtained from the Central Institute for Experimental Animals (Kawasaki, Japan). The donor pigs, Seoul National University (SNU) miniature pigs (Kim et al., 2009. Xenotransplantation. 16:11-18), were bred in a barrier-sustained pathogen-free conditions at the animal facility of the Center for Animal Resource Development, SNU College of Medicine. Experiments were performed after receiving approval from the Institutional Review Board of SNU College of Medicine and the Institutional Animal Care and Use Committee of the Institute of Laboratory Animal Resources, SNU. Islet recipients were Rhesus macaques (*Macaca mulatta*) maintained at the SNU Hospital Non-human Primate Center. The age of the recipients ranged from 48 to 60 mo, and their weight ranged from 4.5 to 5.5 kg. This study was conducted as approved by the SNU Hospital Animal Care and Use Committee and according to the National Institutes of Health guidelines Example 1

Example 1-1

Animals

Animas used were as described above.

Example 1-2

Preparation of Monoclonal Antibody

Human PBMCs were isolated from bloods from healthy donor using concentration gradient centrifuge under Ficoll-Paque™ (GE Healthcare, USA). ICAM-1/Fc proteins were prepared as below. First, mRNAs were extracted using the PBMCs isolated as above which were treated with plant origin haemagglutinin and cDNAs were synthesized by PCR using the following primers encoding NheI and EcoRI restriction site at each ends: Forward primer 5'GCT AGC GCA ACC TCA GCC TCG CTATGGCTC-3' (SEQ ID NO: 1); Reverse primer, 5'-GAA TTC ATC TCA TAC CGG GGG GAG AGC AC-3' (SEQ ID NO: 2).

To fuse human IgG Fc region, the amplified products were cloned into EcoRI and XhoI sites of a vector pSecTag (Invitrogen, USA). Then, the vector was transfected into HEK293 cells (ATCC® CRL-1573) using calcium phosphate methods to express the cloned gene. Then ICAM-1/Fc proteins were isolated from the medium using protein G column.

Then 100 μg of the purified protein emulsified in complete Freund was administered intraperitoneally to a female Balb/c mouse (6-8 weeks, 17~25 g; KOATECH) twice with an interval of two weeks. After two weeks, the immunized mice were boosted with 100 μg of ICAM-1/Fc proteins. Then 3 days after the last administration, the spleen was removed from the mouse to prepare the splenocytes.

Monoclonal antibodies were produced by fusing the spleen cells of Balb/c immunized with human ICAM-1/Fc with SP2/0-Ag14 mouse myeloma cells (ATCC® CRL-1581) resistant to 9-azaguanine. Cell fusion was performed basically following the method described in Koeler and Milstein (Koeler & Milstein Nature, 1975, 256, 495-497). Briefly $10^8$ spleen cells were fused with $10^7$ myeloma cells using 50% polyethylene glycol 4000 (Roche, USA). The cells were then washed once PBS and resuspended in Dulbecco's modified Eagle's medium (DMEM) containing 20% fetal bovine serum (FBS), 100 μM hypoxanthine, 0.44 μM aminopterin and 16 μM thymidine (HAT media, Sigma). The cells were seeded onto each well of four 96-well plates and incubated at 37° C. in a 5% $CO_2$ incubator for two weeks and allowed to form colonies.

Then when colonies were formed after two weeks, the supernatants were screened for the expression of antibodies using human ICAM-1-transfected HEK 293T cells. Wild-type HEK293T cells were used as a negative control. The harvested media were incubated with HEK293T cells for 30 min at 4° C., which were then washed with PBS containing 0.05% Tween. Then the cells were stained with FITC-conjugated anti mouse IgG antibody for 30 min at 4° C. and then colonies stained with the antibody compared to the negative control were selected and subcloned 0.5 cell per well by limited dilution to produce a stable hybridoma clone producing the monoclonal antibody. Among the hybridomas produced, hybridomas producing an antibody binding to ICAM-1 from monkey and human were obtained and deposited as KCLRF-BP-00264 on May 4, 2011 with KCLRF (Korean Cell Line Research Foundation).

Example 1-3

Mapping the Binding Domain of Anti-Human ICAM-1 Monoclonal Antibody

To identify the ICAM1 domain for MD-3 antibody binding, human and mouse ICAM1 genes were obtained from N. Hogg (Cancer Research UK, London, England, UK). The monkey ICAM-1 gene was cloned based on the published sequence (available from GenBank/EMBL/DDBJ under accession no. NM_001047135.1). The chimeric constructs as described in FIG. 1A were cloned according to a previously described protocol (Berendt et al., 1992. Cell. 68:71-81). HEK 293T cells were then transfected with plasmid DNAs constructed and the cells were stained with primary antibody at 4° C. for 30 min. After washing in PBS with 0.05% Tween® 20 and staining with FITC-conjugated anti-mouse Ig antibody at 4° C. for 30 min, the live cells, gated as the propidium iodide (Sigma-Aldrich)-negative population, were analyzed using FACSCalibur™ (BD) equipped with CellQuest Pro™ software (BD).

Results are shown in FIG. 1A which is the result of the binding assay between MD-3 and HEK293 cells transfected with vector alone or vector encoding domains 1, 2, or 3-5 of human (h) or mouse (m) ICAM-1 and MD-3 binding assessed by flow cytometry. As shown in FIG. 1A, from the difference in the binding affinity of the antibody to Chimera #1 (hD1-mD2-mD3-5) and Chimera #2 (hD1-hD2-mD3-5), MD-3 was found to bind specifically to domain 2 of ICAM-1 and showed no cross reactivity to mouse ICAM-1.

Example 1-4

Adhesion Assay of Anti-Human ICAM-1 Monoclonal Antibody to Cells

The effect of MD-3 on the adhesion of leukocytes to endothelial cells was examined. ICAM-1 mediates leukocyte-leukocyte and leukocyte-endothelial cell interactions by binding to LFA-1 (lymphocyte function associated antigen 1) and Mac-1. Therefore, antibodies to ICAM-1 or LFA-1 are able to prevent the adhesion of leukocyte to endothelial cells and T cell activation. HUVECs (Human Umbilical Vein Endothelial Cell) were prepared and cultured on hydrated collagen gels (for monocyte adhesion) or directly on fibronectin-coated 96-well plates (for neutrophil adhesion), as described previously (Muller et al., 1989. J. Exp. Med. 170:399-414). As controls, anti CD-18 antibody (IB4 monoclonal antibody) (Wright et al., 1983. Proc. Natl. Acad. Sci. USA. 80:5699-5703) and conventional ICAM-antibody (R6-5-D6) (Smith et al., 1988. J. Clin. Invest. 82:1746-1756; Berendt et al., 1992. Cell. 68:71-81) were used.

Figure 1B:
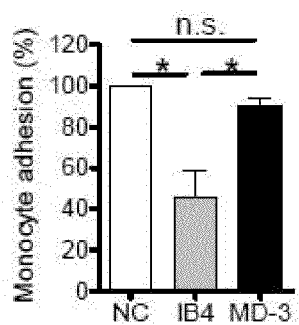
Figure 1B:
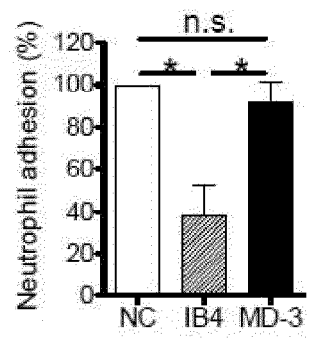
Figure 1B:
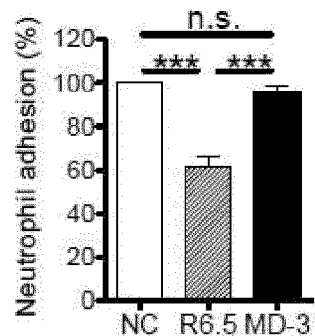

For neutrophil adhesion, HUVEC monolayers were activated by culturing them in 10 ng/ml TNF overnight. HUVECs were not activated for monocyte adhesion assays. Under these conditions, when freshly isolated PBMCs are added, lymphocytes do not stick to the endothelial cells, but monocytes do (Muller and Weigl, 1992. J. Exp. Med. 176:819-828). Neutrophils (Lou et al., 2007. J. Immunol. 178:1136-1143) and PBMCs (Muller and Weigl, 1992. J. Exp. Med. 176:819-828) were isolated as described previously and subjected to adhesion assays using the standard approaches (Muller and Weigl, 1992; Lou et al., 2007; Muller and Luscinskas, 2008 Methods Enzymol. 443:155-176). In brief, freshly isolated polymorphonuclear neutrophils or PBMCs were resuspended at $1 \times 10^6$ cells/ml or $2 \times 10^6$ cells/ml, respectively, mixed gently with monoclonal antibodies as shown in FIG. 1B at a final concentration of 20 μg/ml, and added to the endothelial monolayers for 25 min at 37° C. Monolayers were washed free of nonadherent cells, fixed, and stained with Wright-Giemsa stain for microscopic evaluation. Six replicates of each variable were performed for each experiment.

Results are shown in FIG. 1B in which PBMCs or neutrophils were incubated with human umbilical vein endothelial monolayers in the absence (negative control [NC]) or presence of monoclonal antibodies specific for CD18 (IB4), ICAM-1 (R6.5) or MD-3. Data are expressed as the mean adhesion relative to control±SE of three experiments (except IB4 in the monocyte adhesion assay, where n=2), with six replicates per experiment. n.s., not significant; *, P<0.05; ***, P<0.001. As shown previously, ICAM-1 domain 2 antibody R6.5-D6 and anti-CD18 (IB4) antibody was fond to inhibit the adhesion of leukocytes to endothelial cells. However, MD-3 was not found to inhibit the adhesion of both monocytes and neutrophils to endothelial cells. This indicates that MD-3 does not affect the transendothelial migration of immune cells.

Example 2

Induction of Antigen Specific T Cell Tolerance in Humanized Mouse Using MD-3

Example 2-1

Generation of Humanized Mouse

Humanized mice were generated according to a previously described protocol (Ito et al., 2002. Blood 100:3175-82). In brief, NOG mice were exposed to 200 rad of total body irradiation from a 137Cs source. The next day, each recipient mouse received $1-2 \times 10^5$ CD34+ cells that were purified from human cord blood cells using magnetic sorting (Miltenyi Biotec). Repopulation of total human hematopoietic cells and T cells in peripheral blood was monitored weekly by flow cytometry after staining with anti-human MHC class I and CD3 antibodies. At the time of sacrifice, spleens were collected, and single cells were resuspended in flow cytometry buffer (PBS with 0.1% bovine serum albumin and 0.1% Na azide). After staining with fluorochrome-conjugated antibodies for 30 min at 4° C., the live cells were analyzed using a flow cytometer. The following fluorochrome-labeled monoclonal antibodies were purchased from BD or Dinona: anti-human MHC class I (YG13), CD3 (UCHT1), CD4 (RPA-T4), CD8 (DN17), CD11c (B-ly6), CD14 (MEM-18), CD15 (HI98), CD19 (HIB19), CD80 (L307.4), C86 (FUN-1), and CD123 (9F5).

Figure 2A:
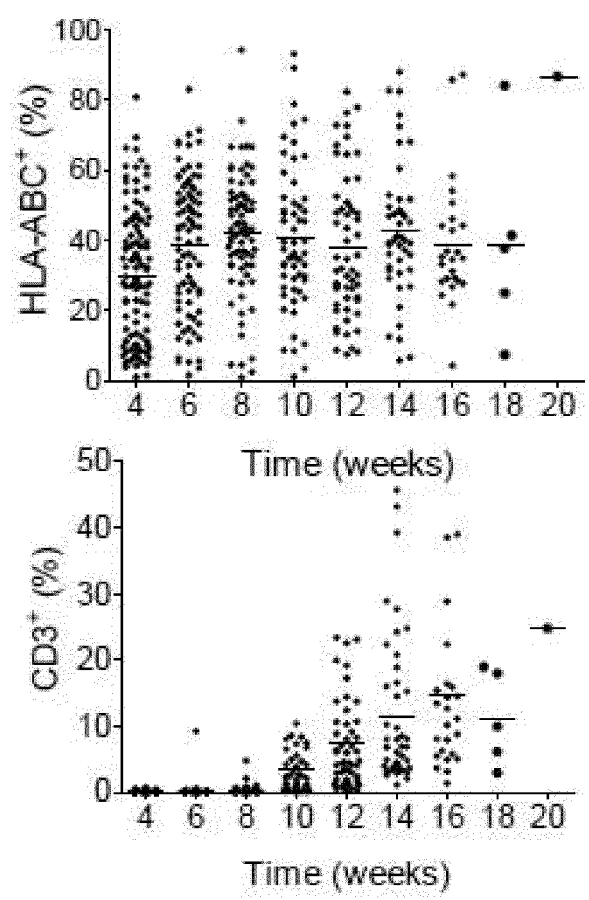
FIGS. 2A to 2C show the results of human hematopoietic cell engraftment and immune cell development in humanized mice.
Figure 2B:
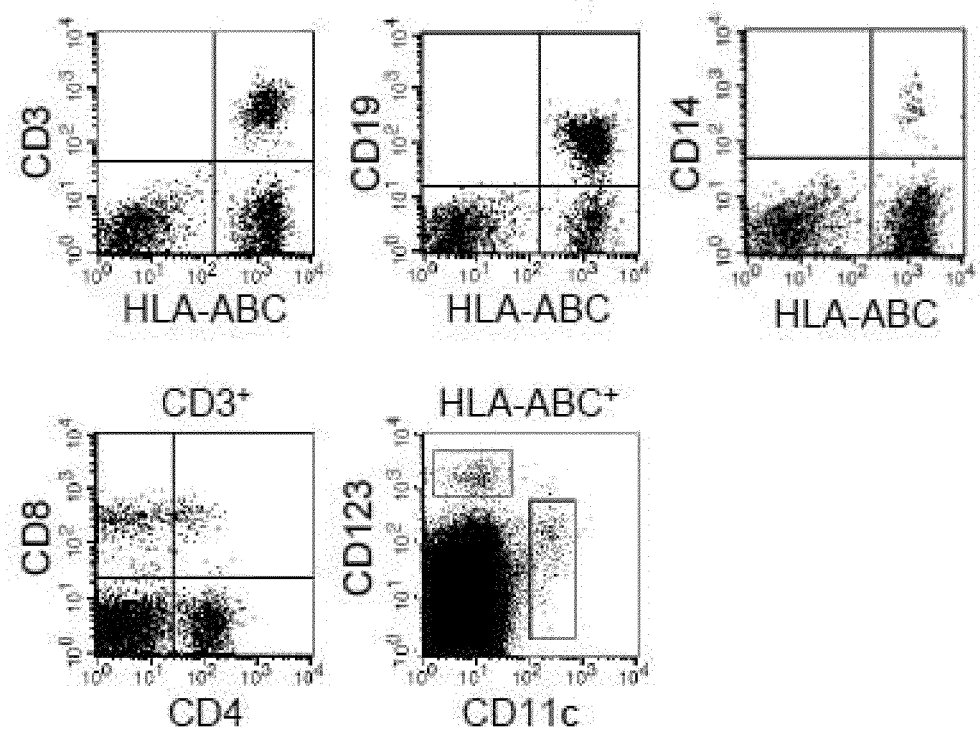
Figure 2C:
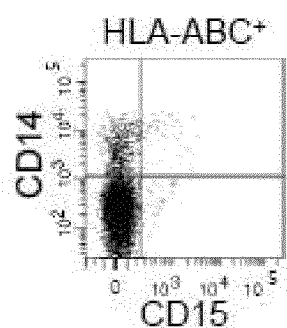

Results are shown in FIGS. 2A to 2C. In FIG. 2A, Data represent the percentage of human HLA-ABC+ or CD3+ cells in the peripheral blood of consecutively analyzed mice at the indicated weeks after transplantation of human CD34+ cells. Cumulative data (n=111) were obtained from >10 independent experiments. Horizontal bars indicate the mean. In FIG. 2B, flow cytometry data show CD4+CD3+ or CD8+ CD3+ T cells, B cells (CD19+), monocytes (CD14+), and conventional (CD11c+) or plasmacytoid (CD123+) DCs in the spleen. Data shown are representative of more than five independent experiments. In FIG. 2C, flow cytometry data show the individual population of CD14+CD15− monocytes and CD14-D15+ neutrophils in the peripheral blood. Shown are representative data from one experiment of two mice. As shown in FIGS. 2A to 2C, it was found that T and B cells are fully repopulated in mouse after about 14 to 16 weeks after the intravenous injection of CD34+ cells from human cord blood Example 2-2

Porcine Pancreas Procurement and Islet Isolation

A total pancreatectomy was performed without warm ischemia time, and islet isolation was performed using the modified Ricordi method, as previously described (Jin et al., 2010. Cell Transplant. 19:299-311). In brief, Liberase MTF C/T (Roche) or CIzyme™ collagenase MA and CIzyme™ BP protease (VitaCyte) were dissolved in endotoxin-free water and diluted to a total volume of 1 ml/g of pancreas weight with a preservation solution at 4° C. and intraductally administered. The preservation solution was composed of Na hydroxide, potassium hydroxide, calcium chloride, magnesium sulfate, Na phosphate, d-mannitol, and NaCl. During digestion, the pancreas, which was inflated with collagenase, was incubated without shaking for 12-15 min at 35-37° C. until the pancreas tissue was loosened. This was followed by manual shaking with serial sampling. After free islets were observed in the serial sample, digestion was stopped by cooling to 4° C. and exposing the islets to 10% porcine serum. Islets were purified with a continuous OptiPrep™ density gradient (Axis-Shield) and a Cobe 2991 cell separator (Gambro BCT Inc.). Purified islets were cultured overnight in Medium 199 (Invitrogen) supplemented with 10% porcine serum, 10 mM nicotinamide (Sigma-Aldrich), and 1% penicillin-streptomycin at 37° C.

Example 2-3

Porcine Islet Grafts in Humanized Mice

Diabetes was induced by high dose i.v. STZ (total of 200 mg/kg, split into two doses separated by 24 h), and mice with fasting glucose levels >250 mg/dl were considered diabetic. 7 d later, isolated porcine islets (5,000 IEQs/mouse) were transplanted under the kidney capsule. Peripheral blood was sampled weekly from the retroorbital sinus to monitor blood glucose levels using a portable glucometer (Accu-Chek®; Roche), and porcine C-peptide levels in serum were determined by radioimmunoassay (Linco) according to the manufacturer's protocol. A successful engraft was defined as porcine C-peptide >0.5 ng/ml, and graft rejection was defined as the day of C-peptide <0.1 ng/ml. Rejection was confirmed by histological analysis of the grafts.

Example 2-4

Induction of Type 1 Diabetes in Nonhuman Primates

A central venous catheter (5Fr. Dual-Lumen PICC; Bard Access System) was inserted into the right internal jugular vein in monkeys under general anesthesia. Monkeys were fasted overnight and were prehydrated with normal saline (0.9% NaCl, 40-60 ml/kg/day i.v.) via a tether system for 12 h before STZ (USB Co.) administration to reduce adverse nephrotoxic effects. Butorphanol or metoclopramide was also administered to prevent chemically induced vomiting caused by the STZ.

A high dose of STZ (110-120 mg/kg) was diluted with 10 ml normal saline and given i.v. within 5 min. Additional hydration with normal saline was given for 2-4 h. Blood glucose levels were measured using a portable glucometer (Accu-Chek®) or a continuous glucose monitoring system (Guardian RT; Medtronic Inc.). STZ was administered in the morning, and a light meal was given to the monkeys in the afternoon. If there was a loss of appetite, dextrose was infused via a tether system to prevent hypoglycemia. Liver and kidney function tests were performed before and after STZ administration, and C-peptide levels were assessed by radioimmunoassay (Linco) according to the manufacturer's protocol.

After successfully inducing type 1 diabetes, blood glucose levels were checked at least two or three times per day, and hyperglycemia was controlled by s.c. injecting human recombinant insulin such as Humalog® (Eli Lilly), Novolin® N (Green cross, Korea), or Lantus® (Sanofi-Aventis). Fasting and nonfasting blood glucose levels were maintained in the diabetic monkeys at approximately <150 mg/dl (>8.3 mmol/l) and <200 mg/dl (11.1 mmol/l), respectively.

Complete type 1 diabetes was confirmed by persistent hyperglycemia and <0.2 ng/ml of C-peptide levels based on the i.v. glucose tolerance test. In brief, after an overnight fast and no insulin, 0.5 g/kg of 50% dextrose solution added to same volume of normal saline was infused i.v. for 1 min. Blood glucose levels were measured in monkeys before and 2, 5, 15, 30, 60, 90, and 120 min after infusion. Insulin and C-peptide levels were measured at the same time intervals.

Example 2-5

Islet Transplantation into Nonhuman Primates

All monkeys were fasted for 12 h before surgery. After premedicating the monkeys with atropine sulfate (0.04 mg/kg s.c.; Huons), general anesthesia was induced with thiopental Na (25 mg/kg i.v.; JWP) and maintained with 1% isoflurane, $N_2O$, and $O_2$. Lactated Ringer's solution or 5% dextrose saline was administered i.v. during the operation. Cefazolin® Na (25 mg/kg i.v.; Chong Kun Dang, Korea) was given prophylactically, and meloxicam (0.2 mg/kg i.v.; Boehringer Ingelheim) was administered for anti-inflammatory and analgesic effects before surgery. A laparotomy was performed, and the jejunal arch was exposed to infuse the islets. A 24- or 22-gauge catheter was inserted through the jejunal vein and approached near the portal vein. The porcine islets were infused with gravity pressure for 8-12 min. After infusion, the vessel was ligated with a 5-0 Prolene® suture. Finally, the abdominal cavity was closed using a common method. After surgery, the tether system was applied for continuous fluid therapy and infusion of low dose sugar, if necessary.

Example 2-6

Elispot Assays

The frequencies of IL-2- or IFN-gamma-secreting antigen specific T cells in spleens of humanized mice and peripheral blood of nonhuman primates were measured using an ELISPOT kit (Mabtech). Anti-IL-2 or IFN-gamma capture antibody-coated plates were washed four times with sterile PBS (200 µl/well) and blocked for 30 min with 10% human serum-supplemented RPMI 1640 media at room temperature. After removing the media, $3 \times 10^5$ splenocytes from the humanized mice or $2.5 \times 10^5$ of PBMCs from nonhuman primates were cultured with $5 \times 10^4$ porcine islet cells in RPMI 1640 media supplemented with 10% human serum for 40 h at 37° C. in a 5% $CO_2$ incubator. For humanized mice, 0.1 mg/ml KLH or T cell-depleted gamma-irradiated $7 \times 10^5$ human PBMCs pooled from three volunteers were also used as stimulators. After the 40-h culture, cells were removed, and the plates were washed five times with PBS (200 µl/well).

Alkaline phosphatase-conjugated detecting antibody diluted at 1:200 or 1:1,000 for IL-2 or IFN-gamma, respectively, in 100 µl PBS containing 0.5% fetal bovine serum was then added and incubated for 2 h at room temperature. The plates were washed five times with PBS, and 100 µl BCIP/NBP substrate was added. Color development was stopped by washing with tap water. The resulting spots were counted on a computer-assisted ELISPOT Reader System (AID).

Example 2-7

Histopathological Examination and Immunohistochemical Staining of Tissue Sections Formalin-fixed, paraffin-embedded tissues were sectioned to a thickness of 4 µm and stained with hematoxylin and eosin (H&E). For immunohistochemistry, formalin-fixed, paraffin-embedded tissue sections were dewaxed in xylene, rehydrated using a graded alcohol series, and incubated in an endogenous peroxidase-blocking solution for 5 min. Antigen retrieval was performed by incubating the sections in 6 mM of citrate buffer at 99° C. for 20 min using the Bond Max system (Leica), and nonspecific staining was prevented by treating the tissue sections with rabbit serum (1% in PBS) for 30 min. Anti-human insulin (Dako), CD3 (F7.2.38; Dako), and CD68 (PG-M1; Dako) antibodies were applied for 30 min, and antibody binding was detected using a VECTASTAIN® Elite ABC kit (PK6101; Vector Laboratories). Microscopic observations were performed with an ECLIPSE® 80i Bright-Field Microscope Set (Nikon) equipped with CFI 10x/22 eyepiece, Plan Fluor objectives (with 4×, 10×, 20×, and 100× objectives) and DS-Fi1 camera. We used NIS-Elements BR 3.1 software (Nikon) for image acquisition.

Example 2-8

Statistical Analysis

All data were analyzed using Prism software (GraphPad Software). Data are presented as mean±SE. Comparison between groups was performed by either Student's t test (two groups) or one-way analysis of variance (multiple groups). Survival data were analyzed by log-rank test. P-values <0.05 were considered significant.

Example 2-9

In Situ Induction of Antigen-Specific T Cell Tolerance by MD-3 Treatment in Humanized Mice Example 2-9-1

Suppression of the Rejection of the Transplanted Tissues by MD-3

Figure 3A:
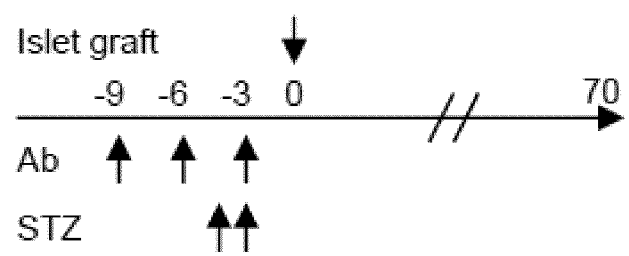
FIGS. 3A to 3D show the assessment of graft survival in humanized mice, in which porcine islets were transplanted under the renal capsule of humanized mice that had been rendered diabetic by STZ or were non-diabetic and received an injection of isotype-matched irrelevant control or MD-3 antibody (Ab).
Figure 3B:
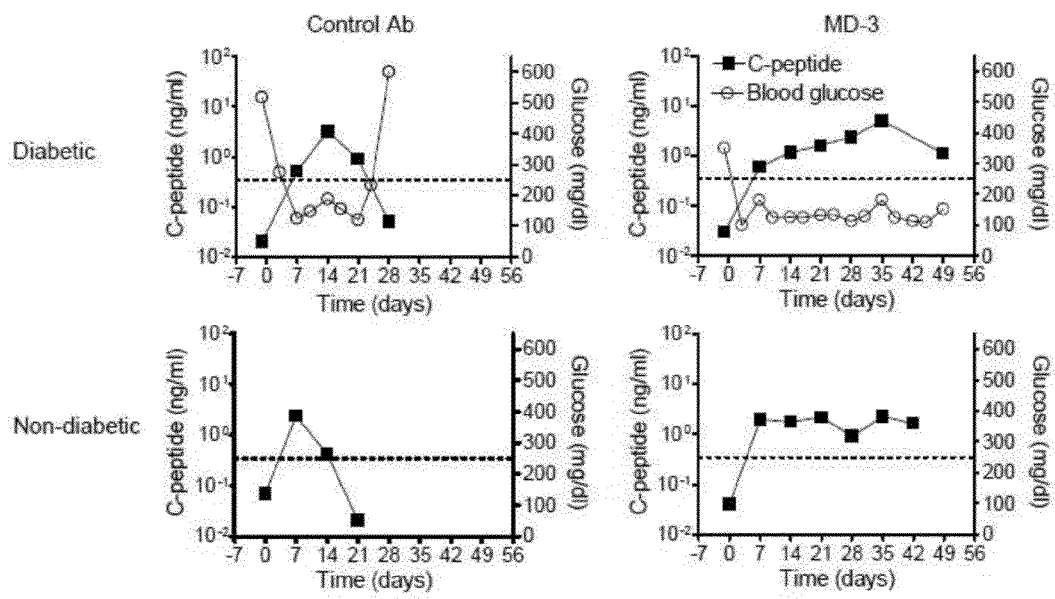
Figure 3C:
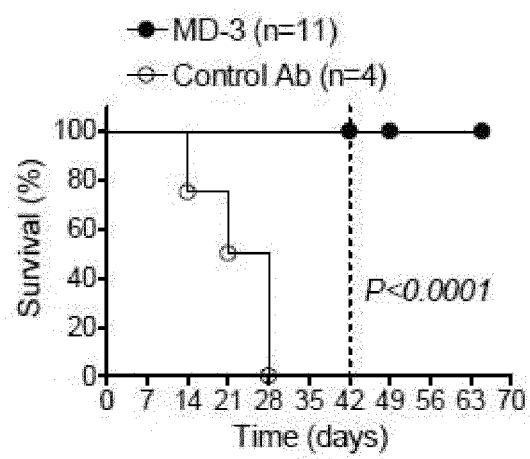

To investigate the induction of T cell tolerance by MD-3, we established a porcine islet xenograft model in humanized mice, which were properly repopulated with human immune cells as shown in FIG. 2 and Examples 2-1 and 2-3. Control animals received an irrelevant IgG1 monoclonal antibody, and the experimental group received MD-3. These two antibodies were injected into mice three times at 3-d intervals (dose 300 µg per mouse) before islet transplantation (FIGS. 3A and 3B [top]). Humanized mice that did not receive STZ before porcine islet transplantation were also examined to exclude any possible effect of STZ on MD-3 antibody function and generalized immune response (FIG. 3B, bottom). Three days after the administration, blood glucose and serum porcine C-peptide levels were monitored weekly (FIG. 3B), and mice were sacrificed 42 days after the initial transplantation (FIG. 3C). FIG. 3A depicts the experimental protocol with time.

Figure 3D:
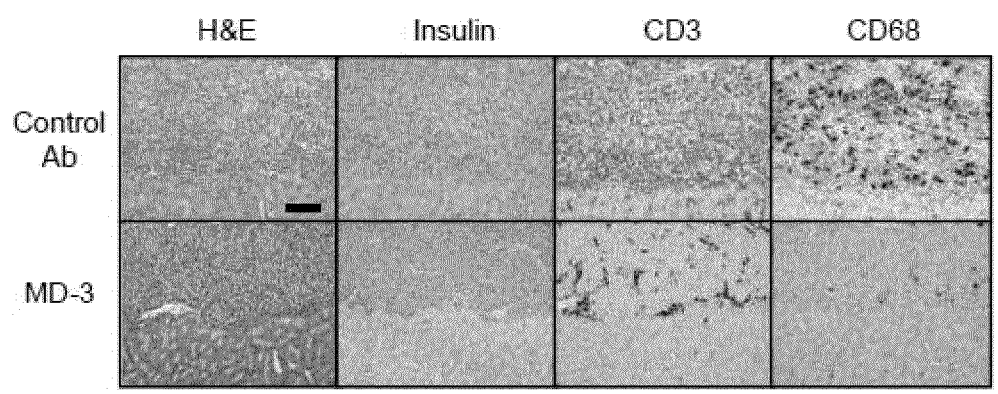

Results are shown in FIGS. 3B to 3D. FIG. 3B shows fasting blood glucose (open circles; right y axis) and porcine C-peptide (closed squares; left y axis) levels which were monitored weekly. During the monitoring period, in the groups treated with MD-3, the blood glucose was maintained at the normal level as well as the amount of C-peptide was detected at the normal level compared to the control. These data indicate the normal secretion of insulin from the transplanted islet. In FIG. 3C, functional survival of islet xenografts was plotted over time based on serum level of porcine C-peptide, The dotted line indicates the day when a portion of the mice were sacrificed for ELISPOT and histopathological analyses. Median graft survival in the control group was 24.5 d. In contrast, animals treated with MD-3 showed no evidence of graft rejection up to the time of their sacrifice. In FIG. 3D, serial kidney sections of a representative mouse in the control or MD-3-treated groups were stained with H&E or antibodies specific for insulin, human CD3, or human CD68. In the control group, insulin-positive porcine islet cells were completely destroyed and replaced by inflammatory infiltrates, in which CD3+ T cells and either CD68+ macrophages were the predominant cellular components. In contrast, in the MD-3-treated group, large nests of insulin-positive porcine islet cells were clearly seen in the subcapsular area of the kidney with negligible infiltration of mononuclear cells in the pen-islet area (FIG. 3D, bottom)

Example 2-9-2

Suppression of Transplantation Rejection by MD-3 Through Induction of Antigen Specific T Cell Tolerance As shown in EXAMPLE 2-9-1, MD-3 treatment resulted in the prolonged survival of xenografts in humanized mice. Thus to confirm that the lack of an immune response was a result of antigen-specific or generalized immunosuppression, two third-party stimulating antigens: a cellular alloantigen and soluble KLH was used for stimulation.

Figure 4A:
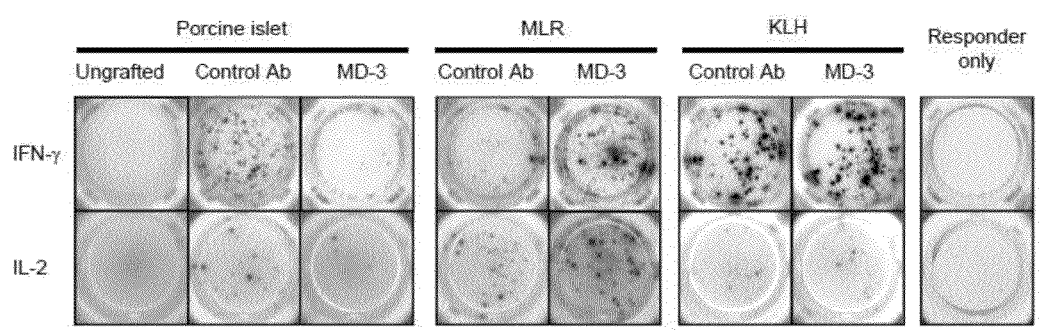
FIGS. 4A and 4B show the induction of antigen-specific T cell tolerance in humanized mice.
Figure 4B:
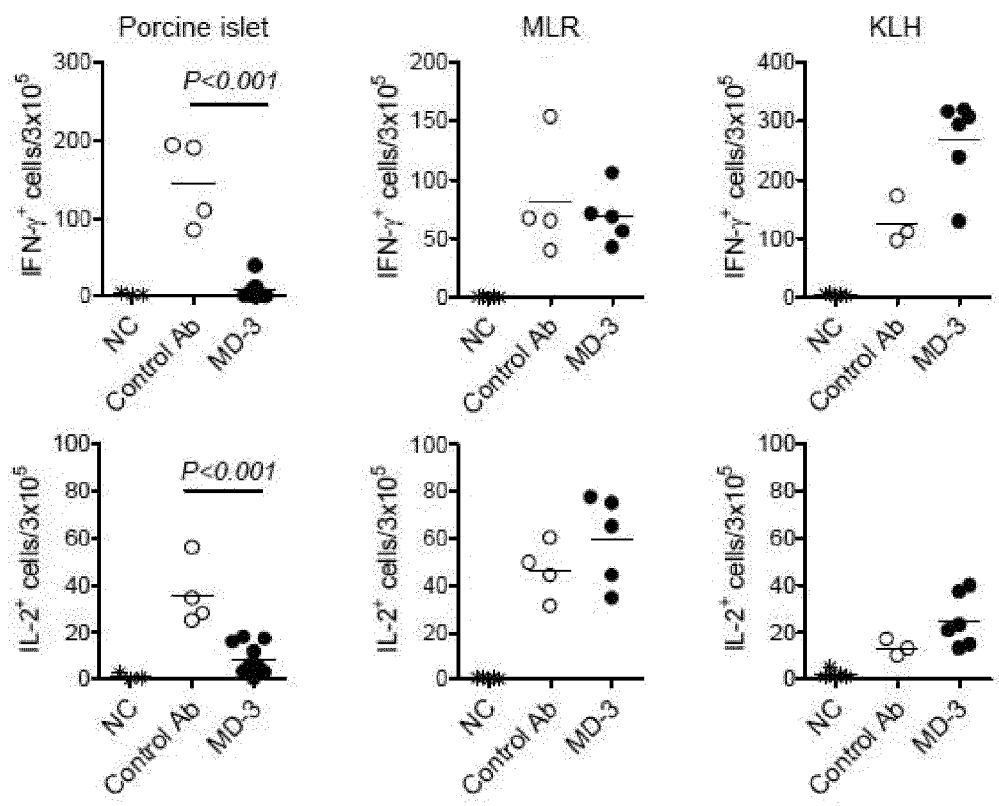

Results are shown in FIGS. 4A and 4B. In FIG. 4A, recipient mice were challenged with KLH at 4 weeks after transplant. Splenocytes were isolated at 6 weeks after transplant and tested for recall IL-2 and IFN-gamma responses against donor islets, human allogeneic blood mononuclear cells (MLR), and KLH by ELISPOT assay. In FIG. 4B, Summarized data from 4-11 mice are presented as total numbers of cytokine-producing cells per $3 \times 10^5$ splenocytes. As a negative control (NC) for anti-islet response, splenocytes from humanized mice that did not undergo transplantation (ungrafted) were stimulated with porcine islets. In contrast, splenocytes from engrafted mice cultured in the absence of stimulating antigen (responder only) were used as a negative control for MLR and anti-KLH responses. Horizontal bars represent mean values. Ab represents antibody.

As shown in FIGS. 4A and 4B, when total splenocytes from control mice were stimulated with porcine islets, significant number of IL-2- and IFN-gamma-secreting T cells were detected (FIGS. 4A and 4B, left). In contrast, IL-2- and IFN-gamma-secreting T cells were almost completely absent from MD-3-treated mice, indicating the complete suppression of T cell responses to xeno-antigens. In contrast, the activation of T cells in response to human alloantigens, as assessed by mixed lymphocyte reaction (MLR), was comparable with that of controls (FIGS. 4A and 4B, middle). These data suggest that the unresponsiveness of the T cells does not reflect generalized immunosuppression, but rather the induction of T cell tolerance specific for porcine islet antigens This induction of antigen-specific T cell tolerance was further indicated by in vivo challenge with an unrelated soluble antigen, KLH. At day 28 after transplantation, at which time MD-3 had been cleared completely, mice were immunized with soluble KLH antigen. Two weeks later, splenocytes were isolated and restimulated with the same antigen in an ex vivo system, and the numbers of KLH-specific T cells were evaluated in an ELISPOT assay. As shown in FIGS. 4A and 4B (right), there was a clear anti-KLH response in MD-3-treated mice in terms of the numbers of cells producing IFN-gamma and IL-2.

In summary, these data again suggest that a normal immune response to KLH occurred in humanized mice that had been tolerized against diverse antigens from grafted porcine islets, indicating that the response was antigen specific.

Example 3

Modulation of Differentiation of DCs by MD-3 In Vivo and In Vitro

Example 3-1

Generation of DC from Monocyte

Human CD14+ monocytes were isolated from healthy volunteers using magnetic sorting, and immature DCs were derived from purified monocytes by culture with 1,000 U/ml GM-CSF (PeproTech) and 1,000 U/ml IL-4 (PeproTech) in the absence or presence of 10 µg/ml of antibodies, as described previously (Subklewe et al., 1999. EBNA-3A vaccinia virus. Blood. 94:1372-1381) and were matured on day 6 by adding 5 µg/ml LPS (Sigma-Aldrich) after washing. The next day, the cells were harvested for flow cytometry, and the cytokine concentration in the culture supernatant was measured by Cytometric Bead Array (BD). The following fluorochrome labeled monoclonal antibodies were purchased from BD or Dinona: anti-human MHC class I (YG13), MHC class II (L243), CD11c (B-ly6), CD80 (L307.4), C86 (FUN-1), and CD40 (5C3).

Example 3-2

Preparation of Human CD11e Antibody-Saporin Immunotoxin (IT)

To produce the anti-human CD11c antibody-saporin IT, saporin was purchased from Sigma-Aldrich, and saporin conjugation of antibody was performed as described previously with some modifications (McGraw et al., 1994 Cancer Immunol. Immunother. 39:367-374). In brief, anti-human CD11c antibody was activated with N-succinimidyl-3-(2-pyridyldithio)-propionate, conjugated with thiolated saporin, and added to N-ethylmaleimide to block unreacted sulfhydryl groups. After removing the unconjugated saporin by protein G affinity chromatography, the anti-CD11c-saporin complexes were eluted with ImmunoPure elution buffer (Thermo Fisher Scientific) and dialyzed against PBS. The possibility of contamination by free saporin was ruled out by SDS-PAGE.

Example 3-3

Modulation of Differentiation of Human DCs by MD-3

Figure 5A:
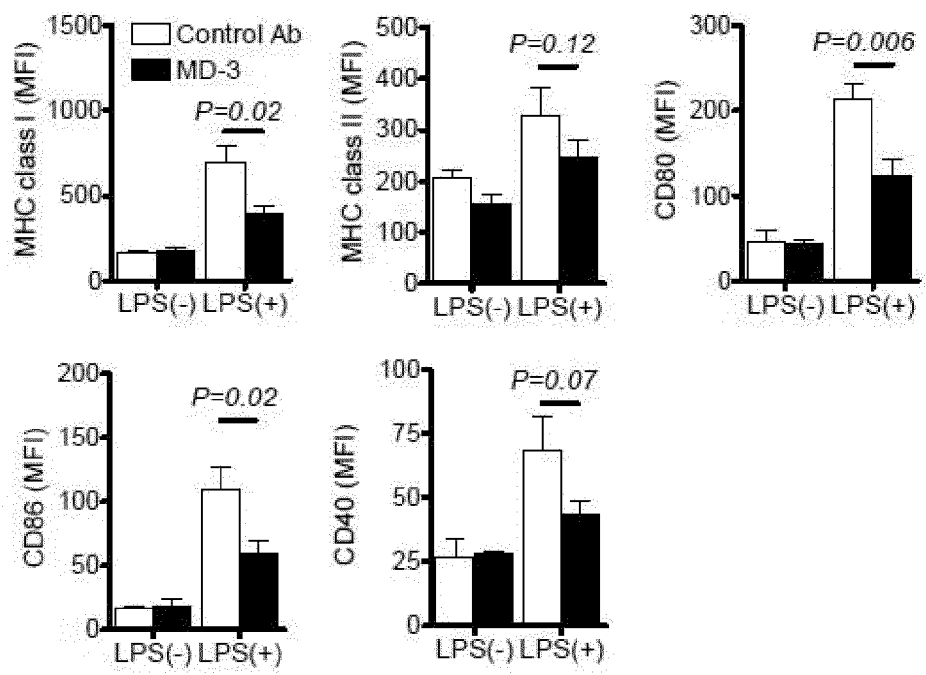
FIGS. 5A to 5C show the results of the arrest of DC maturation at the semimature stage in which immature monocyte-derived DCs were generated from human CD14+ monocytes by incubation with GM-CSF and IL-4 in the presence of MD-3 or isotype-matched control antibody (control Ab) from the beginning of culture and after 6 d, DCs were stimulated or not with LPS.
Figure 5B:
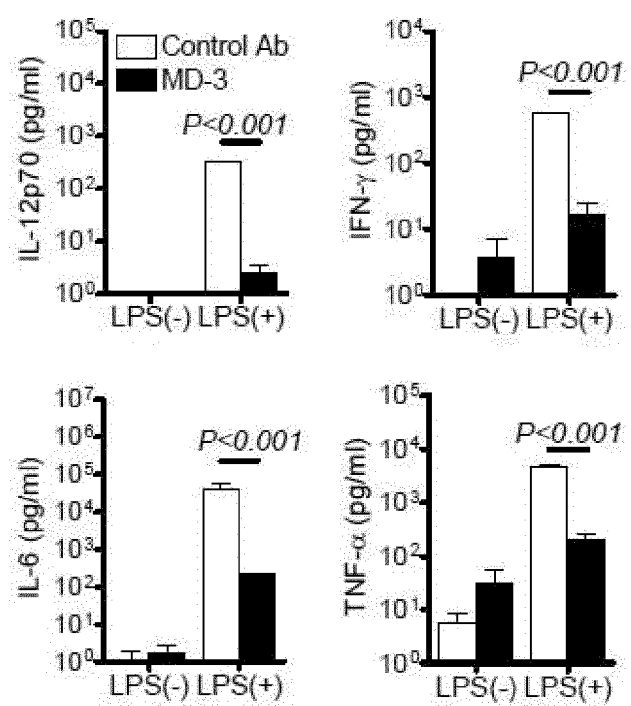

To investigate the effect of MD-3 on modulating the maturation status of human monocyte derived DCs, differentiation from monocytes to DCs was induced as described in EXAMPLE 3-1. Human CD14+ monocytes, isolated as precursors of monocyte derived DCs, were incubated for 6 d with GM-CSF and IL-4, in the presence of MD-3 or a control antibody, to induce their differentiation into immature DCs. Subsequently, immature DCs were treated with the Toll-like receptor agonist, LPS (maturation signal), for 1 day and then analyzed for cytokine production and surface expression of molecules linked to antigen presentation Results are shown in FIGS. 5A and 5B. In FIG. 5A, expression levels of MHC class I and II, CD80, CD86, and CD40 on their surface were compared by flow cytometry. Cumulative data showing mean fluorescent intensity (MFI)±SE of MHC class I and II, CD80, CD86, and CD40 were obtained from four independent experiments. FIG. 5B shows representative cytokine levels in the culture supernatants of immature and LPS-treated monocyte-derived DCs in the presence of MD-3 or control antibody. Results are the mean±SE of triplicate cultures, and data are representative of three independent experiments.

As shown in FIGS. 5A and 5B, treatment of monocytes with MD-3 from the beginning of culture resulted in the arrest of DC maturation in a semimature state. This differentiation state was confirmed by the expression of surface molecules, such as MHC classes I & II, CD80, CD86, and CD40, at levels between those of immature and mature DCs (FIG. 5A). Furthermore, the production of cytokines, notably IL-12p70, IFN-gamma, IL-6, and TNF, was significantly lower in MD-3-treated cells than in those treated with the control antibody (FIG. 5B). The phenotype and function of DCs treated with MD-3 during their maturation were consistent with the features of semimature or tolerogenic DCs. Thus, these in vitro results suggest that MD-3 alone can arrest DC maturation in a semimature state.

Figure 5C:
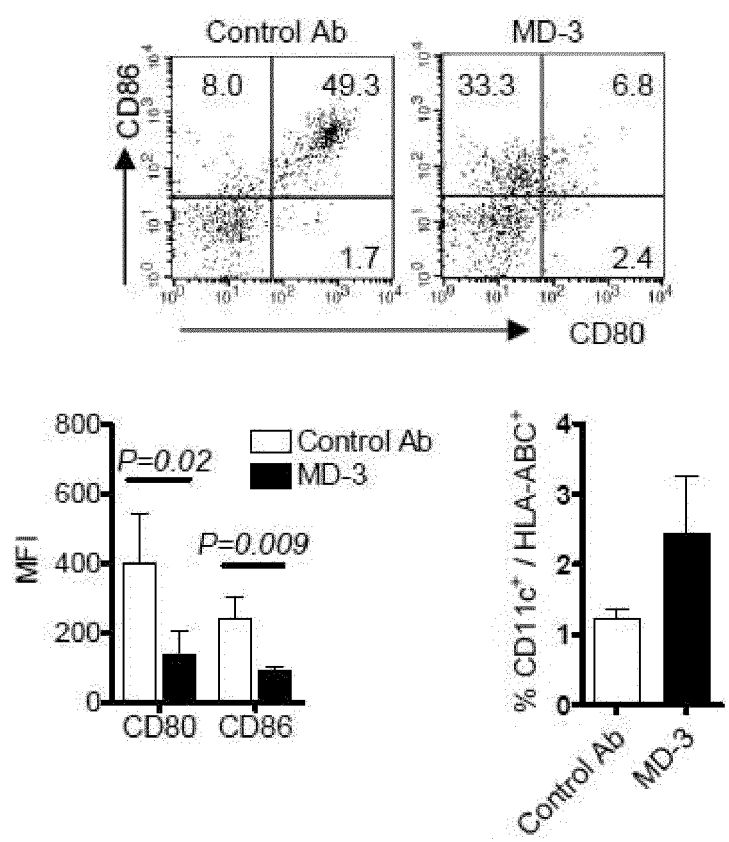

Next, to analyze the effect of MD-3 on DC maturation status in vivo, MD-3 and control antibodies were injected into humanized mice three times at 3-d intervals and followed by treatment with LPS. In FIG. 5C, at 24 h after LPS treatment, splenocytes were stained with HLA-ABC, CD11c, CD80, and CD86 antibodies. Representative dot plots of CD80 and CD86 expression on gated CD11c+ DCs are shown at the upper panel. Numbers indicate the percentage of cells in each quadrant. Cumulative data (n=3) showing mean fluorescent intensity were obtained from three independent experiments (lower left). The percentages of CD11c+ cells among HLA-ABC+ cells in spleens were also calculated (lower right). Error bars indicate SE. As shown in FIG. 5C, the expression of both surface molecules CD80 and CD86 was reduced in DCs from MD-3-treated mice versus the control group. These in vivo results, together with the aforementioned in vitro data, suggest that this form of maturation arrest can be achieved through in vivo treatment with MD-3 alone.

Further since ICAM-1 is expressed on vascular endothelial cells, as well as activated T and B cells, changes in the surface expression of MHC and co-stimulatory molecules and the production of inflammatory cytokines in HUVECs and activated T cells and (b) antibody production in activated B cells were determined, when treated with MD-3 antibody. In HUVECs, no differences in surface expression and cytokine production of control and MD-3-treated groups (not depicted) were found.

Example 3-4

Role of DCs in Antigen Specific T Cell Tolerance Induced by MD-3

Figure 6A:
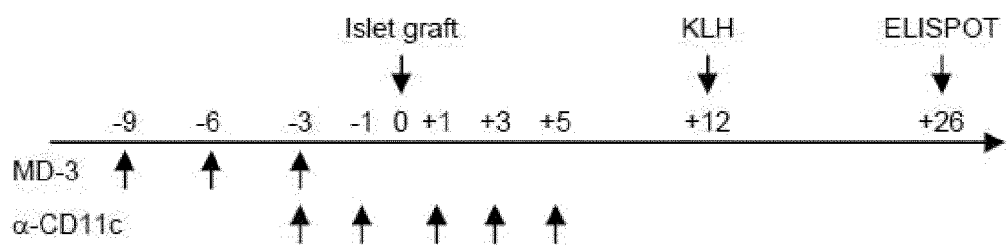
FIGS. 6A to 6D show the abrogation of T cell tolerance induction after DC ablation in which humanized mice received anti-CD11c immunotoxin (alpha-CD11c; 5 μg/mouse) or PBS every other day from 3 d before porcine islet transplantation up to the fifth day after transplant (D+5). These mice were then immunized with KLH on the 12th day after transplant (D+12).

To confirm that DCs play a key role in the induction of antigen-specific tolerance in vivo, saporin-conjugated anti-CD11c immunotoxin (IT) prepared as in EXAMPLE 3-2 was administered into humanized mice to establish a DC-depleted mouse model, which were then used for the experiment. Experimental scheme is depicted in FIG. 6A. Humanized mice received anti-CD11c IT (alpha-CD11c; 5 µg/mouse) or PBS every other day from 3 d before porcine islet transplantation up to the fifth day after transplant (D+5). These mice were then immunized with KLH on the 12th day after transplant (D+12).

Figure 6B:
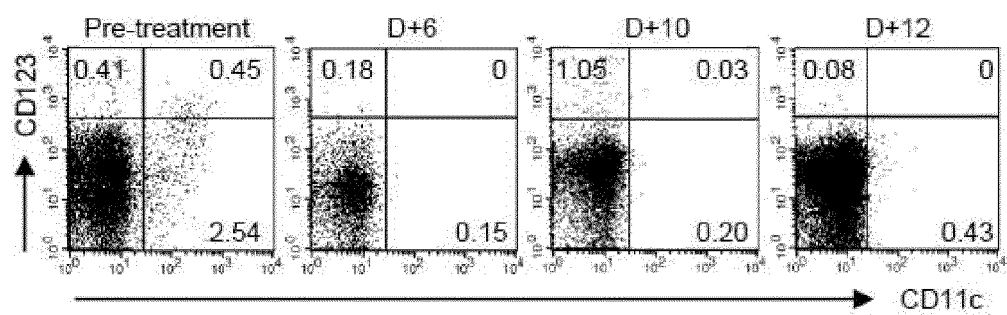

Results are shown in FIGS. 6A to 6D. FIG. 6B is a result from flow cytometric analysis on the indicated days after islet transplantation to assess depletion of CD11c+DCs in the spleen of humanized mice. Intraperitoneal injection of anti-CD11c IT nearly completely ablated DCs in humanized mice up to 10 d after islet graft. Serum MD-3 levels were measured two times per week, and MD-3 was not detected at 7 d after transplantation.

Figure 6C:
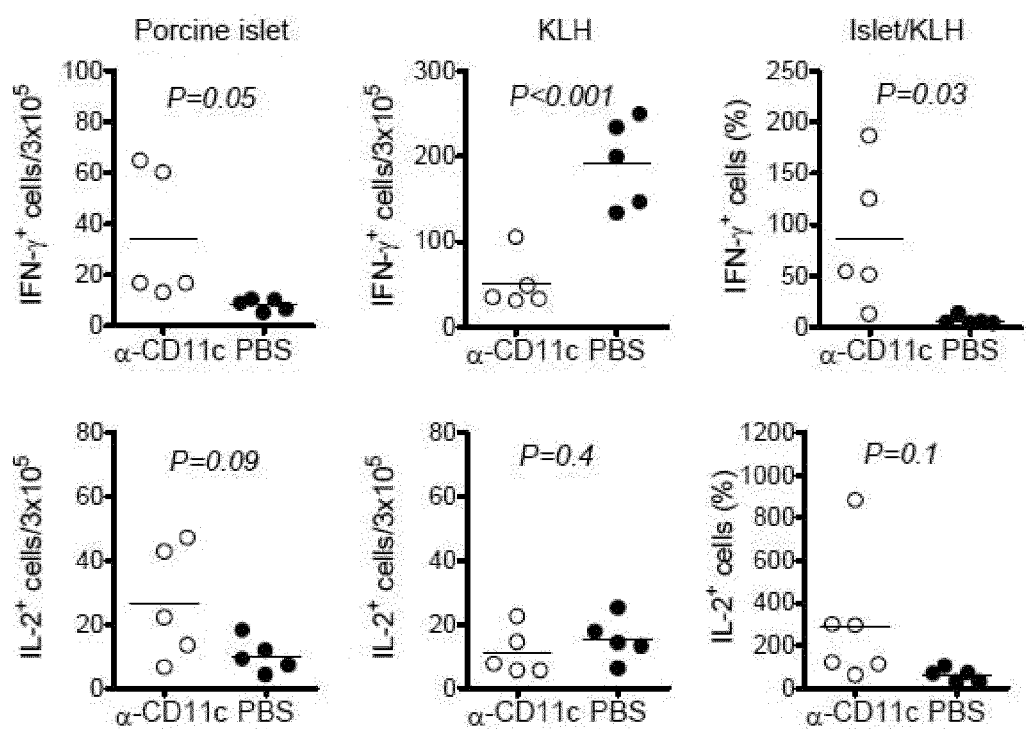
Figure 6D:
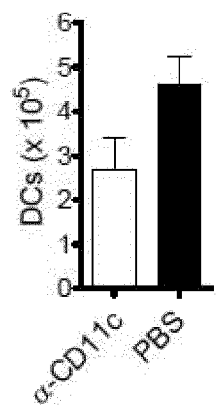

At 12 d after transplantation, both groups of humanized mice were immunized with a mixture of alum and KLH. Splenocytes were isolated 14 d after KLH immunization and tested for recall IL-2 and IFN-gamma responses via ELISPOT assay against donor islets and KLH. Results are shown in FIG. 6C. The data from individual mice are presented as total numbers of cytokine producing cells per $3 \times 10^5$ splenocytes or normalized anti-islet response (Islet/KLH) by dividing the anti-islet spot number by the anti-KLH spot number in each mouse. Horizontal bars represent mean values. As shown in FIG. 6C, 26 days after transplantation, numbers of IL-2- and IFN-gamma secreting T cells after rechallenge of porcine islet cells ex vivo differed significantly between control and DC-ablated mice. Ablation of CD11c+ DCs at the time of xenoantigen challenge resulted in severe impairment of T cell tolerance whereas mice treated with MD-3 alone mounted a T cell tolerance to xenoantigen challenge (FIG. 6C, left).

Next, to confirm that the T cell response that had returned against islet antigens was caused by the recovery of a normal immune response, which had been lost via the ablation of DCs, T cell responses to KLH in the control (PBS treated) and experimental group (IT treated) were examined. As shown in FIG. 6C (middle), both groups exhibited clear T cell responses to KLH. However, in these experiments, numbers of KLH-responding T cells were reduced in anti-CD11c IT-treated mice, probably because of actual decreases in the numbers of DCs present in their spleens (FIG. 6D), suggesting that there may still have been a low level of toxicity. To normalize the anti-islet immune response based on the individual immune status of the mouse, the number of islet-responding T cells was divided by the number of spots responding to KLH stimuli in each mouse and expressed the relative value as a percentage. As shown in FIG. 6C (right), the data obtained demonstrated a clear difference in the T cell response to islet antigens between the two groups. These results indicate that the induction of antigen-specific T cell tolerance depends primarily on DCs.

Example 4

Induction of Antigen Specific T Cell Tolerance by Treatment with MD-3 in Nonhuman Primates Although humanized mice are powerful tools for exploring the functions of T and B cells and DCs, there are certain limitations when extrapolating humanized mouse data to humans. This includes the lack of granulocytic series, NK cells, and other as of yet unidentified factors (Shultz et al., 2007. Nat. Rev. Immunol. 7:118-130). Therefore, to test whether data from the humanized mouse system could be reproduced in a nonhuman primate model, experiments using Rhesus macaques were performed.

Figure 7A:
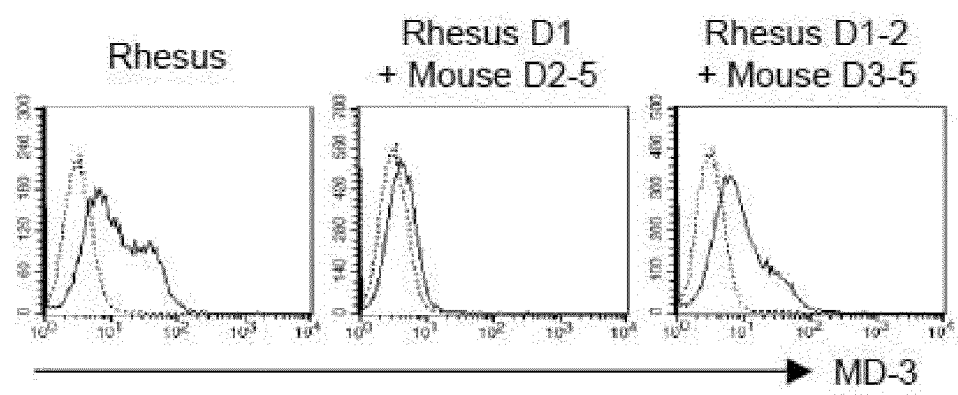
FIGS. 7A to 7C show the induction of T cell tolerance in a nonhuman primate.

MD-3 was found to bind to domain 2 of Rhesus ICAM-1 as shown in FIG. 7A. In FIG. 7A, HEK293 cells were transfected with Rhesus ICAM1 gene or chimeric genes of Rhesus and mouse ICAM-1, and MD-3 binding was assessed by flow cytometry (solid line). As the negative control (dotted line), the cells were stained with only FITC-conjugated secondary antibody.

Then as described in EXAMPLES 2-4 and 2-5, adult porcine islets (50,000 IEQs/kg) were intraportally transplanted into three Rhesus monkeys (R043, R042, and R038) that pretreated with MD-3 antibody.

Figure 7B:
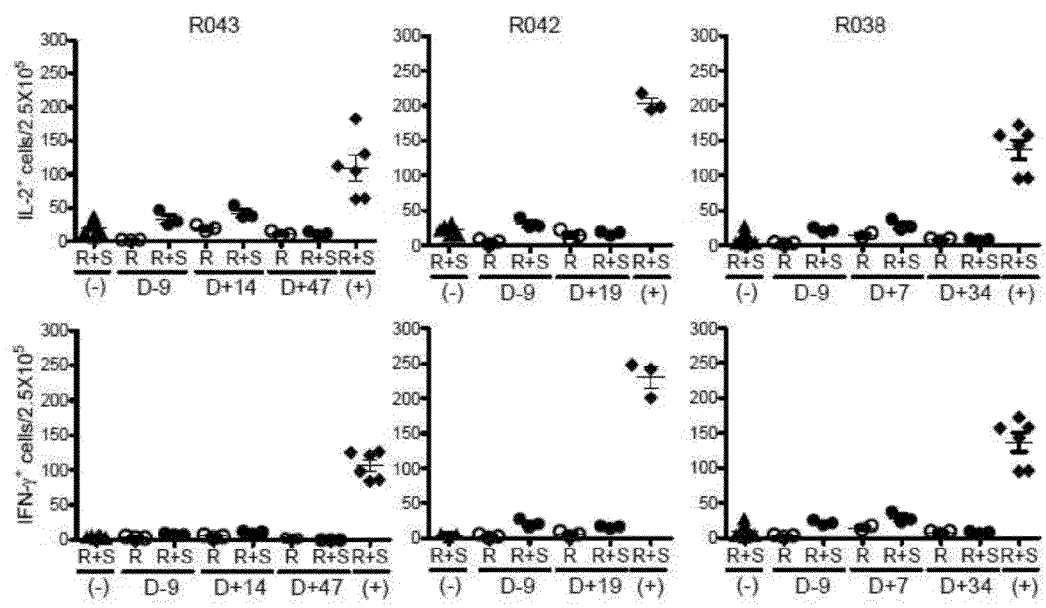
Figure 7C:
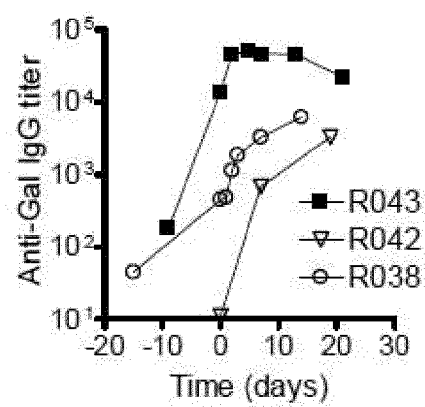

Results are shown in FIG. 7B. In FIG. 7B, adult porcine islets (50,000 IEQs/kg) were intraportally transplanted into three Rhesus monkeys (R043, R042, and R038) that received MD-3 antibody alone. PBMCs were isolated on the indicated days after transplantation, and the frequency of T cells secreting IL-2 or IFN-gamma in response to donor islets was determined by ELISPOT assay. Results are presented as numbers of cytokine producing cells per $2.5 \times 10^5$ PBMCs in each triplicate culture. MD-3 monotherapy failed to achieve graft survival for >9 d, whereas ELISPOT analysis of PBMCs isolated from three recipient monkeys revealed near-complete suppression of IFN-gamma and IL-2 responses to donor pig islet antigen from day 7-47 (FIG. 7B). This clearly indicates that the induction of T cell tolerance to porcine islets was achieved, while immune reactions which is not dependent on T cell is involved in graft rejection. FIG. 7C in which anti-Gal IgG levels were measured at the indicated time before and after porcine islet transplantation via ELISA shows that anti-Gal (galactose-alpha-1,3-galactose) which is a typical T cell independent antibody was increased in Rhesus serum which received MD-3 antibody alone before the porcine islet transplantation.

Long-term graft survival was finally achieved with a combination treatment of low-dose rapamycin (trough level 6-12 μg/ml) and chimeric anti-CD154 blocking antibody (5C8; National Institutes of Health), as well as MD-3. This combined therapy of rapamycin and chimeric anti-CD154 antibody were known to regulate NK and NK-mediated innate B cell activation, which has been reported to be related to T-independent antigens, such as galactose-alpha-1,3-galactose (Gal) and non-Gal sugar antigens (Li et al., 2007. Blood. 110:3926.3935).

Figure 8A:
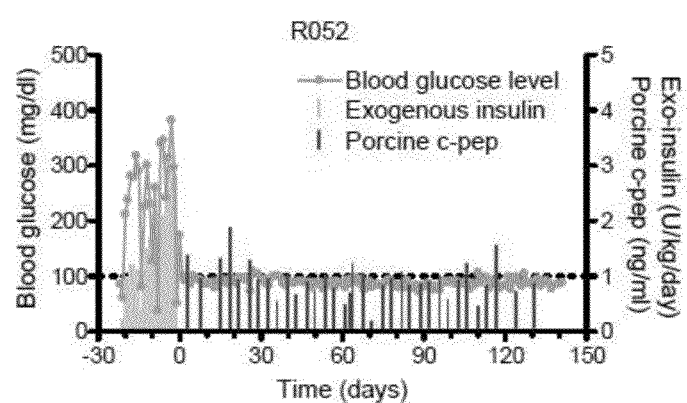
FIGS. 8A to 8C show the achievement of long-term survival of a porcine islet xenograft in a nonhuman primate via combination therapy including MD-3.
Figure 8A:
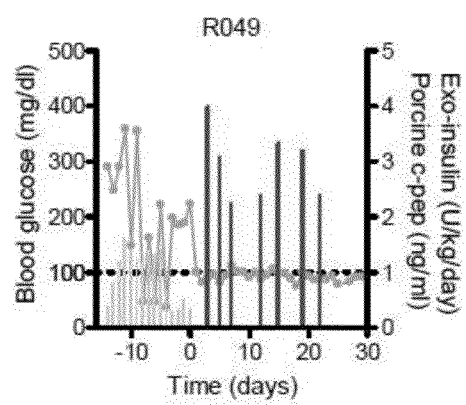
Figure 8B:
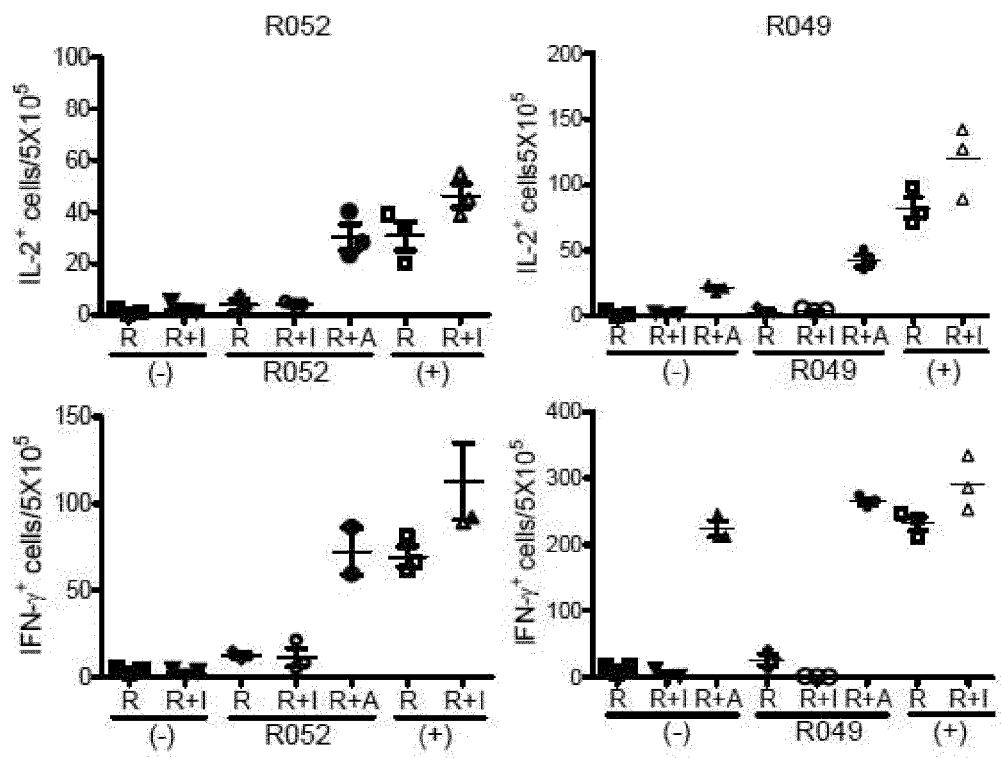
Figure 8C:
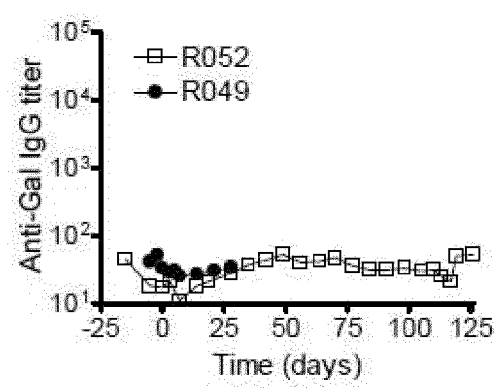

FIGS. 8A to 8C shows the achievement of long-term survival of a porcine islet xenograft in a nonhuman primate via combination therapy including MD-3. In FIG. 8A, after successfully inducing type 1 diabetes in Rhesus monkey via STZ administration, hyperglycemia was controlled by s.c. injecting human recombinant insulin (Exotic insulin). Adult porcine islets (100,000 IEQs/kg) were intraportally transplanted into Rhesus monkeys (R052 and R049) that received MD-3 combined with rapamycin and anti-CD154 antibody. Blood glucose level and serum porcine C-peptide concentration were measured at the indicated time after porcine islet transplantation. Such combination therapy using MD-3 in combination with anti-CD154 antibody and rapamycin, resulted in porcine islet graft survival for >140 days by now as well as normal glucose level and high level of C-peptide concentration.

In FIG. 8B, PBMCs were isolated at 127 and 7 days after transplantation from R052 and R049, respectively, and the frequency of T cells secreting IL-2 or IFN-gamma in response to donor islets (I) or allogeneic PBMCs (A) was determined by ELISPOT assay. Results are presented as numbers of cytokine-producing cells per $5 \times 10^5$ PBMCs in each triplicate culture. R, responder cells only; R+I, responder cells stimulated with porcine islet cells; R+A, responder cells stimulated with allogeneic PBMCs; (−), unsensitized monkeys as a negative control; (+), sensitized monkeys as a positive control. Error bars indicate SE. In FIG. 8C, Anti-Gal IgG levels were measured at the indicated time before and after porcine islet transplantation via ELISA.

Two monkeys (R052 and R049) again maintained xenoantigen-specific T cell tolerance as shown by suppression of IFN-gamma and IL-2 responses to donor pig islet antigens, whereas an intact immune response to a third party of alloantigen was maintained (FIG. 8B).

Example 5

Long Term Survival of Porcine Islet Graft in Nonhuman Primates by Treatment with Chimeric MD-3

In the Examples hereinbefore, mouse MD-3 antibody was used. In the Examples below MD-3 chimeric antibody was developed for clinical application and the efficacy was tested on nonhuman primates.

Example 5-1

Preparation of Human IgG4 Chimeric MD-3 Antibody

Total RNA was extracted from MD-3 hybridoma cells using the RNeasy® Mammalian total RNA Miniprep kit (QUIAGEN). Reverse-transcription PCR was achieved using the following primers: VH (Forward: 5'-TGGGCCCTTG-GTGGAAGCTGAGGAGACT GTGAGAGCGGTGC-CTTG-3' (SEQ ID NO: 3); Reverse: 5'-CTTGGTGGAA CTGA GGAGACTGTGAG-3' (SEQ ID NO: 4)); VL (Forward: 5'-TATTTCCAGCTTGGTCC CCCCTCCGAACGT-GTACGGAAAATGTGTATT-3' (SEQ ID NO: 5); Reverse: 5'-CC GTTTTATTTCCAGCTTGGT-3' (SEQ ID NO: 6)).

For cloning human IgG4 gene, total RNA was extracted from human PBMC using the RNeasy Mammalian total RNA Miniprep kit (QUIAGEN). Reverse-transcription PCR was achieved using human IgG4 heavy chain primer as follows: VH (Forward: 5'-CAAGGCACCGCTCTCACAGTCTCCT-CAGCTTCCACCAAGGGCCC A-3' (SEQ ID NO: 7); Reverse: 5'-GCGGCCGCTCATTTACCCAGAGA-CAGGGA GAGGCTCTTCTGTGTGTA-3' (SEQ ID NO: 8)); or for human lambda light chain primer (Forward: 5'-TTCGGAGGGGGGACCAAGCTG-GAAATAAAACGGCAGCCC AAGGCTGCC-3' (SEQ ID NO: 9), Reverse:5'-GCGGCCGCCTATGAACATTCTGTA GGGGCCACTGTCTTCTCCACGGT-3' (SEQ ID NO: 10)).

The heavy chain chimeric gene containing MD-3 $V_H$ region and human IgG4 constant region and light chain chimeric gene containing MD-3 $V_L$ region and human lambda constant region genes were achieved using overlap PCR using the following primers: MD-3 VH Region Forward: 5'-CTC-GAGATGGGTTGGAGCTGTATCATCT TCTTTCTGG-TAGCAACAGCT-3' (SEQ ID NO: 11), VH Reverse: 5'-TGGGCCCTTG GTGGAAGCTGAGGAGACTGT-GAGAGCGGTGCCTTG-3' (SEQ ID NO: 12), IgG4 Constant Forward: 5'-CAAGGCACCGCTCTCACAGTCTCCT-CAGCTTCCACCAAG GGCCCA-3' (SEQ ID NO: 13), IgG4 Constant Reverse primer: 5'-GCGGCCGCTCA TTTACCCAGAGACAGGGAGAGGCTCT-TCTGTGTGTA-3' (SEQ ID NO: 14) and MD-3 VL Region Forward: 5'-GGTTCCACTGGTGACTCTAATCTC-GAGATGAAGT TGCCTGTTAGG-3' (SEQ ID NO: 15), MD-3 VL Region Reverse: 5'-TATTTCCAGC TTGGTC-CCCCCTCCGAACGTGTACGGAAAATGTGTATT-3' (SEQ ID NO: 16), Lamda Constant Region Forward: 5'-TTCGGAGGGGGGACCAAGCTGGAAATAAAA CGGCAGCCCAAGGCTGCC-3' (SEQ ID NO: 17), Lamda Constant Region Reverse: 5'-GCGGCCGCCTATGAACAT-TCTGTAGGGGCCACTGTCTTCTCCACGGT-3' (SEQ ID NO: 18).

Figure 9A:
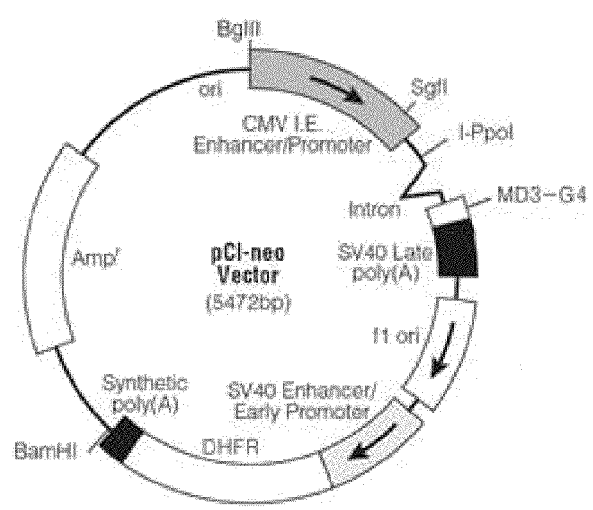
FIG. 9A represents a map of the vector used as in EXAMPLE 5 to prepare MD-3 chimera antibody.
Figure 9B:
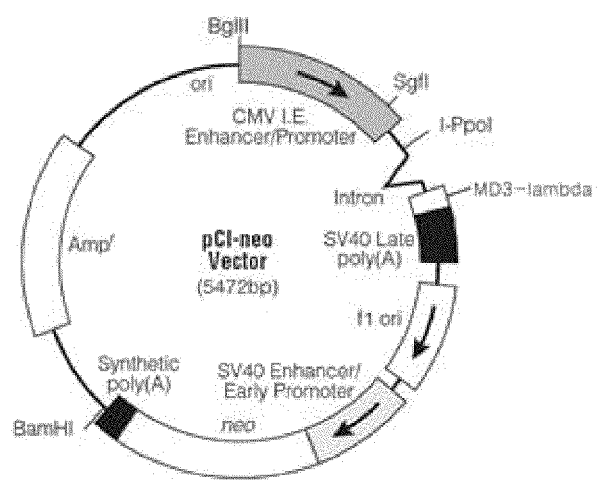
FIG. 9B represents a map of the vector used as in EXAMPLE 5 to prepare MD-3 chimera antibody.

The heavy chain and light chain chimeric genes were cloned in pGEM®-T easy vector with the TA Cloning® kit (Promega, USA.) and sequenced. We replaced neomycin resistant gene was replaced with DHFR gene in pCI-neo vector containing heavy chain chimeric gene as shown in FIGS. 9A and 9B.

Cloning products were digested by XhoI/NotI for heavy chain chimeric gene inserted in pCI-DHFR mammalian expression vector (Promega, USA.) and XhoI/NotI for light chain chimeric gene inserted in pCI-neo vector. Constructions were verified by sequencing.

CHO-DG44 cells, which are dhfr negative, were purchased from Invitrogen (Carlsbad, USA). The cells were maintained in alpha-MEM media with ribonucleoside and deoxyribonucleosides (GIBCO) supplemented with 7% fetal bovine serum (FBS) (GIBCO, USA). CHO-DG44 cells were transfected with the pCI plasmid using Effectene® transfection reagent kit (QIAGEN, Germany). The day before transfection, CHO-DG44 Cells were seeded to 2 ml in 6-well plates at a density of $2\times10^5$ cell/ml in alpha-MEM with ribonucleosides and deoxyribonucleosides media containing 7% FBS and grown overnight. At the day of transfection, 10 μl Effectene® transfection reagent was added to DNA-enhancer mixture (0.4 μg plasmid DNA in 100 μl EC buffer and 3.2 μl enhancer). The mixture of plasmid DNA and Effectene® transfection reagent solution were added in 6-well plates, in which CHO-DG44 cells were seeded at the day before transfection, and the plates were incubated at 37° C. After 3 days, supernatant was tested with ELISA.

Stably transfected cells were selected in FBS-supplemented alpha-MEM media lacking ribonucleosides and deoxyribonucleosides, which prevent cells lacking dhfr from growing. Selected cells were adapted in PowerCHO2 media (for suspension culture; Lonza, USA) without dialyzed FBS but with 1000 nM methotrexate (MTX) for heavy chain transfected cells, 400 μg/ml G418 for light chain transfected cells. Subcloning was accomplished by plating 10,000 cells per 60 mm dish in semi-solid media (ClonaCell®-CHO CD media, STEMCELL TECHNOLOGIES, Canada). After culture more than 10 days, single colonies were harvested and transferred to 96 well plate containing PowerCHO™2 media without dialyzed FBS. After screening the clones for antibody production, cells were seeded in the Erlenmeyer flasks at concentration of $4\times10^5$ viable cells/ml in PowerCHO™2 media. After adaptation, the cells were cultured in bioreactor (Bellocell® 500 culture system, CESCO Bioengineering. Taiwan) and antibody was purified from the culture supernatants using protein G column. The binding activity of the chimeric antibody was tested using human ICAM-1 transfected 293 cells via flow cytometry.

Example 5-2

Prolonged Survival of Porcine Islet Xenograft in Nonhuman Primates Via Injection of MD-3 Chimeric Antibody To test whether MD-3 chimeric antibody as prepared in EXAMPLE 5-1 has a therapeutic efficacy similar to that of original mouse MD-3 antibody, the following xenograft experiments were performed as in EXAMPLE 4 except that chimeric MD-3 was used.

Figure 10A:
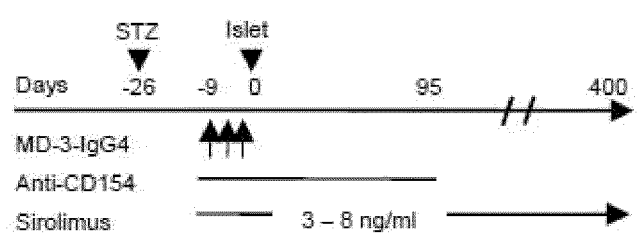
FIGS. 10A to 10D show the long term survival of nonhuman primate Rhesus monkey received porcine islet transplantation via combined therapy including MD-3 chimeric antibody.
Figure 10B:
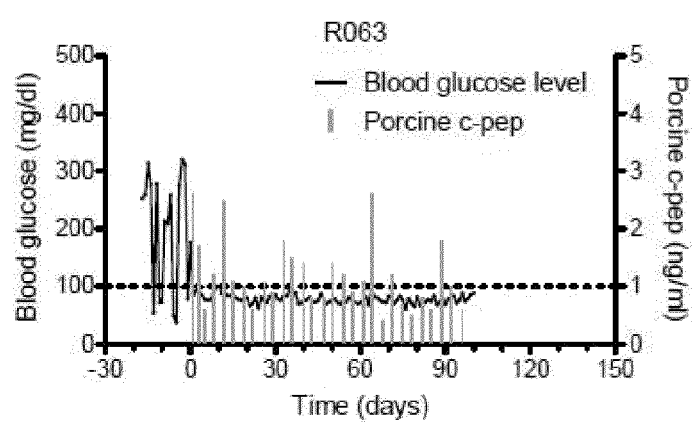
Figure 10C:
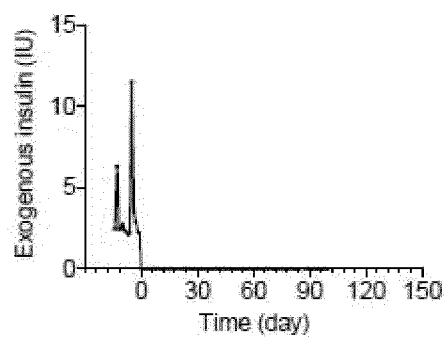
Figure 10D:
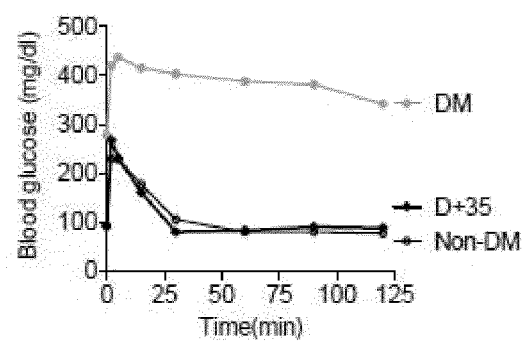

Specifically as shown in FIG. 10A, for an induction therapy, 8 mg/kg MD-3 chimeric antibody was administered to diabetic Rhesus macaque receiving porcine islet transplantation on postoperative days (PODs) −9, −6, and −3. Anti-CD154 mAb (20 mg/kg) were given on PODs −10, −7, −4, 0, 3, 10, and then every 7 to 14 days up to POD 90. And for a maintenance therapy, daily sirolimus was given during the follow-up period (FIG. 10A). The Rhesus macaque that received the combined therapy and porcine islet graft has been remained euglycemic and insulin independent for more than 3 months (FIGS. 10B and 10C). C-peptide production and intravenous glucose tolerance testing verified that xenograft was functioning (FIGS. 10B and 10D). This result shows that MD-3 chimeric antibody used in combination with anti-CD154 and sirolimus is able to significantly prolog the survival of porcine islet grafts.

Example 5-3

Prolonged Survival of Monkey Islet Allograft in Nonhuman Primates Via Injection of MD-3 Chimeric Antibody To test whether MD-3 chimeric antibody as prepared in EXAMPLE 5-1 has a therapeutic efficacy similar to that of original mouse MD-3 antibody, the following allograft experiments were performed as in EXAMPLE 4 except that chimeric MD-3 was used and allogenic islets were used and anti-CD154 was not administered. Sirolimus (rapamycin) was administered up to 229 days after the transplantation.

Figure 11A:
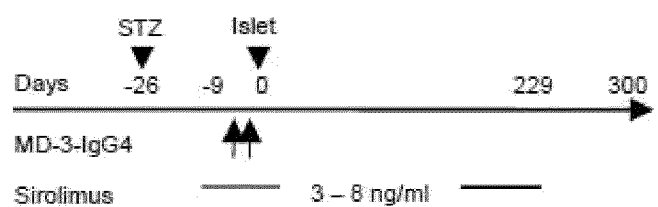
FIGS. 11A to 11D show the long term survival of allogenic islet graft in nonhuman primate Rhesus monkey treated with MD-3 chimeric antibody and sirolimus.

Specifically as shown in FIG. 11A, for an induction therapy, 8 mg/kg MD-3 chimeric antibody was administered to diabetic Rhesus macaque receiving allogenic islet transplantation on postoperative days (PODs) −6, and −3. And for a maintenance therapy, daily sirolimus was administered up to 229 days after the transplantation.

Figure 11B:
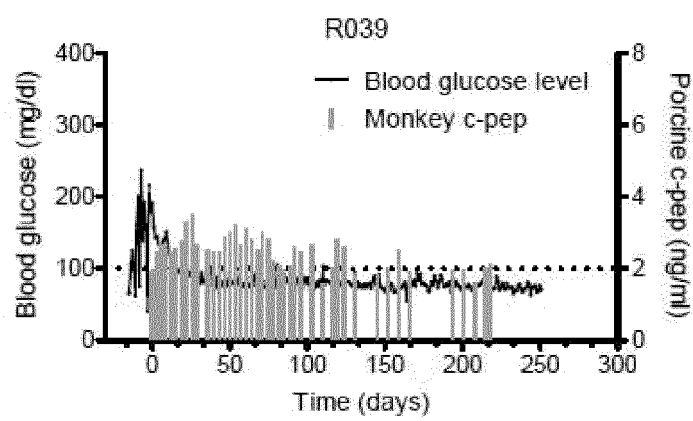
Figure 11C:
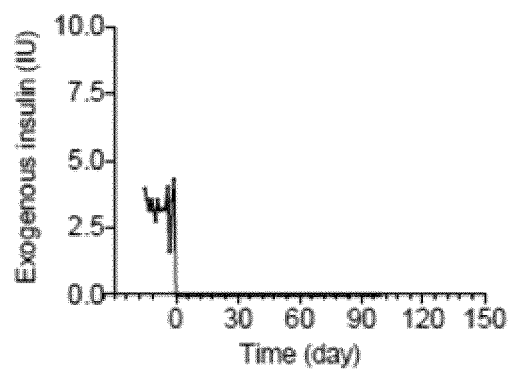
Figure 11D:
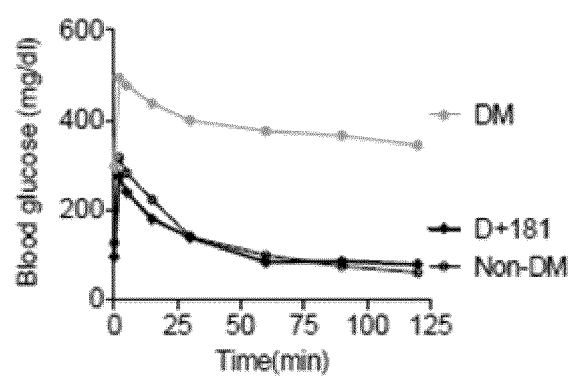

The Rhesus macaque that received the combined therapy and islet graft has been remained euglycemic and insulin independent for more than 9 months (FIGS. 11B and 11C). C-peptide production and intravenous glucose tolerance testing verified that allografts were functioning (FIGS. 11B and 11D). This result shows that MD-3 chimeric antibody, even when the administration of sirolimus was discontinued, is able to dramatically increase the survival period of the islet graft and thus to minimize the amount of immunosuppressant normally used to suppress the rejection of the transplanted tissues or organs.

The various singular/plural permutations may be expressly set forth herein for sake of clarity. Although a few embodiments of the present disclosure have been shown and described, it would be appreciated by those skilled in the art that changes may be made in this embodiment without departing from the principles and sprit of the invention, the scope of which is defined in the claims and their equivalents.

What is claimed is:

1. A monoclonal antibody or an antigen-binding fragment thereof specific for human ICAM-1, the monoclonal antibody comprising: three complementary determining regions (CDRs) from the heavy chain of an antibody produced by the hybridoma cell deposited as accession number of KCLRF-BP-00264 or three CDRs from the light chain of an antibody produced by the hybridoma cell deposited as accession number of KCLRF-BP-00264, or both.

2. The antibody or antigen-binding fragment thereof of claim 1, wherein the antibody comprises two full length heavy chains and two full length light chains.

3. The antibody or the antigen-binding fragment thereof of claim 1, wherein the antigen-binding fragment comprises SCV, ScFv, Fv, Fab, Fab', or F(ab')$_2$.

4. The antibody or the antigen-binding fragment thereof of claim 1, wherein the antibody or the antigen-binding fragment thereof is multi-valent or multi-functional.

5. The antibody or the antigen-binding fragment thereof of claim 1, wherein the antibody or the antigen-binding fragment thereof is a multimer which is formed by two or more of the antibody or antigen-binding fragment thereof which is identical or different being linked to each other.

6. The antibody or the antigen binding fragment thereof of claim 1, wherein the antibody or the antigen-binding fragment thereof is a chimeric form or a humanized form.

7. A method for treating a T-cell mediated immunological disorder or condition comprising administering to a subject in need thereof a pharmaceutical composition comprising the antibody or antigen binding fragment according to claim 1.

8. The method of claim 7, wherein the T-cell mediated immunological disorder or condition is a rejection of a tissue or an organ transplantation rejection, a graft-versus-host disease, or an autoimmune disease.

9. The method of claim 8, wherein the tissue or the organ transplantation includes a pancreatic islet transplantation.

10. The method of claim 8, wherein the tissue or the organ use for the transplantation is an allogenic or xenogenic origin.

11. The method of claim, wherein the pharmaceutical composition further comprises one or more immune regulatory agent selected from the group consisting of rapamycin, an anti-CD154 antibody, and an anti-CD40 antibody.

12. A method for producing an antibody specific for ICAM-1 comprising incubating a hybridoma cell deposited as accession number of KCLRF-BP-00264, and purifying the antibody.

13. A method for maintaining a dendritic cell in a semi-mature state comprising contacting the antibody or the antigen-binding fragment thereof according to claim 1 with an immature dendritic cells in vitro.

* * * * *

SEQUENCE LISTING

<160> NUMBER OF SEQ ID NOS: 18

<210> SEQ ID NO 1
<211> LENGTH: 30
<212> TYPE: DNA
<213> ORGANISM: Artificial Sequence
<220> FEATURE:
<223> OTHER INFORMATION: Forward primer

<400> SEQUENCE: 1
gctagcgcaa cctcagcctc gctatggctc                30

<210> SEQ ID NO 2
<211> LENGTH: 29
<212> TYPE: DNA
<213> ORGANISM: Artificial Sequence
<220> FEATURE:
<223> OTHER INFORMATION: Reverse primer

<400> SEQUENCE: 2
gaattcatct cataccgggg ggagagcac                 29

<210> SEQ ID NO 3
<211> LENGTH: 45
<212> TYPE: DNA
<213> ORGANISM: Artificial Sequence
<220> FEATURE:
<223> OTHER INFORMATION: VH Forward primer

<400> SEQUENCE: 3
tgggcccttg gtggaagctg aggagactgt gagagcggtg ccttg       45

<210> SEQ ID NO 4
<211> LENGTH: 27
<212> TYPE: DNA
<213> ORGANISM: Artificial Sequence
<220> FEATURE:
<223> OTHER INFORMATION: VH Reverse primer

<400> SEQUENCE: 4
cttggtggaa gctgaggaga ctgtgag                   27

<210> SEQ ID NO 5
<211> LENGTH: 48
<212> TYPE: DNA
<213> ORGANISM: Artificial Sequence
<220> FEATURE:
<223> OTHER INFORMATION: VL Forward primer

<400> SEQUENCE: 5
tatttccagc ttggtccccc ctccgaacgt gtacggaaaa tgtgtatt    48

<210> SEQ ID NO 6
<211> LENGTH: 21
<212> TYPE: DNA
<213> ORGANISM: Artificial Sequence
<220> FEATURE:
<223> OTHER INFORMATION: VL Reverse primer

<400> SEQUENCE: 6
ccgttttatt tccagcttgg t                                              21

<210> SEQ ID NO 7
<211> LENGTH: 45
<212> TYPE: DNA
<213> ORGANISM: Artificial Sequence
<220> FEATURE:
<223> OTHER INFORMATION: VH Forward primer

<400> SEQUENCE: 7
caaggcaccg ctctcacagt ctcctcagct tccaccaagg gccca                    45

<210> SEQ ID NO 8
<211> LENGTH: 47
<212> TYPE: DNA
<213> ORGANISM: Artificial Sequence
<220> FEATURE:
<223> OTHER INFORMATION: VH Reverse primer

<400> SEQUENCE: 8
gcggccgctc atttacccag agacagggag aggctcttct gtgtgta                  47

<210> SEQ ID NO 9
<211> LENGTH: 48
<212> TYPE: DNA
<213> ORGANISM: Artificial Sequence
<220> FEATURE:
<223> OTHER INFORMATION: human lambda light chain Forward primer

<400> SEQUENCE: 9
ttcggagggg ggaccaagct ggaaataaaa cggcagccca aggctgcc                 48

<210> SEQ ID NO 10
<211> LENGTH: 47
<212> TYPE: DNA
<213> ORGANISM: Artificial Sequence
<220> FEATURE:
<223> OTHER INFORMATION: human lambda light chain Reverse primer

<400> SEQUENCE: 10
gcggccgcct atgaacattc tgtaggggcc actgtcttct ccacggt                  47

<210> SEQ ID NO 11
<211> LENGTH: 48
<212> TYPE: DNA
<213> ORGANISM: Artificial Sequence
<220> FEATURE:
<223> OTHER INFORMATION: MD-3 VH Region Forward primer

<400> SEQUENCE: 11
ctcgagatgg gttggagctg tatcatcttc tttctggtag caacagct                 48

<210> SEQ ID NO 12
<211> LENGTH: 45
<212> TYPE: DNA
<213> ORGANISM: Artificial Sequence
<220> FEATURE:

```
<223> OTHER INFORMATION: MD-3 VH Reverse primer

<400> SEQUENCE: 12
tgggcccttg gtggaagctg aggagactgt gagagcggtg ccttg          45

<210> SEQ ID NO 13
<211> LENGTH: 45
<212> TYPE: DNA
<213> ORGANISM: Artificial Sequence
<220> FEATURE:
<223> OTHER INFORMATION: IgG4 Constant Forward primer

<400> SEQUENCE: 13
caaggcaccg ctctcacagt ctcctcagct tccaccaagg gccca          45

<210> SEQ ID NO 14
<211> LENGTH: 47
<212> TYPE: DNA
<213> ORGANISM: Artificial Sequence
<220> FEATURE:
<223> OTHER INFORMATION: IgG4 Constant Reverse primer

<400> SEQUENCE: 14
gcggccgctc atttacccag agacagggag aggctcttct gtgtgta       47

<210> SEQ ID NO 15
<211> LENGTH: 45
<212> TYPE: DNA
<213> ORGANISM: Artificial Sequence
<220> FEATURE:
<223> OTHER INFORMATION: MD-3 VL Region Forward primer

<400> SEQUENCE: 15
ggttccactg gtgactctaa tctcgagatg aagttgcctg ttagg          45

<210> SEQ ID NO 16
<211> LENGTH: 48
<212> TYPE: DNA
<213> ORGANISM: Artificial Sequence
<220> FEATURE:
<223> OTHER INFORMATION: MD-3 VL Region Reverse primer

<400> SEQUENCE: 16
tatttccagc ttggtccccc ctccgaacgt gtacggaaaa tgtgtatt       48

<210> SEQ ID NO 17
<211> LENGTH: 48
<212> TYPE: DNA
<213> ORGANISM: Artificial Sequence
<220> FEATURE:
<223> OTHER INFORMATION: Lamda Constant Region Foward primer

<400> SEQUENCE: 17
ttcggagggg ggaccaagct ggaaataaaa cggcagccca aggctgcc       48

<210> SEQ ID NO 18
<211> LENGTH: 47
<212> TYPE: DNA
<213> ORGANISM: Artificial Sequence
<220> FEATURE:
<223> OTHER INFORMATION: Lamda Constant Region Reverse primer

<400> SEQUENCE: 18
gcggccgcct atgaacattc tgtaggggcc actgtcttct ccacggt        47
```